US011419888B2

(12) United States Patent
Chapman et al.

(10) Patent No.: US 11,419,888 B2
(45) Date of Patent: *Aug. 23, 2022

(54) COMPOSITION AND METHOD FOR PROMOTING REDUCTION OF HEAT STRESS IN ANIMALS

(71) Applicants: OmniGen Research, L.L.C., Corvallis, OR (US); The Arizona Board of Regents on Behalf of the University of Arizona, Tucson, AZ (US)

(72) Inventors: James D. Chapman, Macon, GA (US); David Calabotta, Quincy, IL (US); Neil E. Forsberg, Corvallis, OR (US); Steven B. Puntenney, Ione, OR (US); Robert Collier, Tucson, AZ (US); Laun Hall, Spanish Fork, UT (US)

(73) Assignees: OmniGen Research, L.L.C., Corvallis, OR (US); The Arizona Board of Regents on behalf of the University of Arizona, Tucson, AZ (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/723,912

(22) Filed: Dec. 20, 2019

(65) Prior Publication Data

US 2020/0138850 A1    May 7, 2020

Related U.S. Application Data

(63) Continuation of application No. 15/234,971, filed on Aug. 11, 2016, now Pat. No. 10,555,964, which is a
(Continued)

(51) Int. Cl.
*A61K 38/47*    (2006.01)
*A61K 31/716*   (2006.01)
(Continued)

(52) U.S. Cl.
CPC .......... *A61K 31/716* (2013.01); *A23K 20/163* (2016.05); *A23K 20/20* (2016.05);
(Continued)

(58) Field of Classification Search
CPC .. A61K 31/715; A61K 31/716; A61K 31/736; A61K 33/06
See application file for complete search history.

(56) References Cited

U.S. PATENT DOCUMENTS

| 3,244,527 A | 4/1966 | Baker et al. |
| 3,939,275 A | 2/1976 | Baile et al. |

(Continued)

FOREIGN PATENT DOCUMENTS

| CN | 103875942 A | 6/2014 |
| EP | 0551331 B1  | 11/1995 |

(Continued)

OTHER PUBLICATIONS

Aguilar-Uscanga et al., "A study of the yeast cell wall composition and structure in response to growth conditions and mode of cultivation," *Letters in Applied Microbiology*, 37:268-274 (Aug. 6, 2003).

(Continued)

*Primary Examiner* — Lakshmi S Channavajjala
(74) *Attorney, Agent, or Firm* — Klarquist Sparkman, LLP

(57) ABSTRACT

Disclosed herein is a method for promoting reduction of heat stress in animals, as well as a composition for use in the disclosed method. The composition comprises a glucan, silica, mineral clay, mannan, and optionally an endoglucanohydrolase, and may be administered to an animal that is susceptible to or suffers from heat stress.

14 Claims, 16 Drawing Sheets

Related U.S. Application Data continuation of application No. PCT/US2015/015692, filed on Feb. 12, 2015.

(60) Provisional application No. 62/000,986, filed on May 20, 2014, provisional application No. 61/939,206, filed on Feb. 12, 2014.

(51) Int. Cl.
```
A61K 31/736    (2006.01)
A61K 45/06     (2006.01)
A61K 35/02     (2015.01)
A61K 31/715    (2006.01)
A61K 33/00     (2006.01)
A61K 35/00     (2006.01)
A23K 20/163    (2016.01)
A23K 20/20     (2016.01)
A23K 20/28     (2016.01)
A61K 33/06     (2006.01)
A23K 50/10     (2016.01)
A23K 50/20     (2016.01)
A23K 50/30     (2016.01)
A23K 50/40     (2016.01)
A23K 50/70     (2016.01)
```

(52) U.S. Cl.
CPC .............. *A23K 20/28* (2016.05); *A23K 50/10* (2016.05); *A23K 50/20* (2016.05); *A23K 50/30* (2016.05); *A23K 50/40* (2016.05); *A23K 50/70* (2016.05); *A61K 31/715* (2013.01); *A61K 31/736* (2013.01); *A61K 33/00* (2013.01); *A61K 33/06* (2013.01); *A61K 35/00* (2013.01); *A61K 35/02* (2013.01); *A61K 38/47* (2013.01); *A61K 45/06* (2013.01)

(56) References Cited

U.S. PATENT DOCUMENTS

| | | |
|---|---|---|
| 3,943,250 A | 3/1976 | Richter et al. |
| 3,961,080 A | 6/1976 | Sugimoto et al. |
| 4,055,667 A | 10/1977 | Linton et al. |
| 4,138,479 A | 2/1979 | Truscheit et al. |
| 4,251,519 A | 2/1981 | Robbins et al. |
| 4,501,634 A | 2/1985 | Yoshimura et al. |
| 4,619,859 A | 10/1986 | Yoshimura |
| 4,714,716 A | 12/1987 | Park |
| 4,729,902 A | 3/1988 | Urman et al. |
| 4,757,040 A | 7/1988 | Guan et al. |
| 4,759,932 A | 7/1988 | Laurent et al. |
| 4,765,992 A | 8/1988 | Geneix et al. |
| 4,835,218 A | 5/1989 | Yoshimura et al. |
| 4,857,512 A | 8/1989 | Wagner et al. |
| 4,916,198 A | 4/1990 | Scheve et al. |
| 4,950,488 A | 8/1990 | Schweitzer et al. |
| 5,032,401 A | 7/1991 | Jamas et al. |
| 5,100,721 A | 3/1992 | Akao |
| 5,140,949 A | 8/1992 | Chu et al. |
| 5,149,549 A | 9/1992 | Beggs |
| 5,165,946 A | 11/1992 | Taylor et al. |
| 5,183,667 A | 2/1993 | Koch |
| 5,192,547 A | 3/1993 | Taylor |
| 5,272,236 A | 12/1993 | Lai et al. |
| 5,278,272 A | 1/1994 | Lai et al. |
| 5,346,963 A | 9/1994 | Hughes et al. |
| 5,407,751 A | 4/1995 | Genske et al. |
| 5,519,009 A | 5/1996 | Donzis |
| 5,527,573 A | 6/1996 | Park et al. |
| 5,639,492 A | 6/1997 | Turk et al. |
| 5,698,599 A | 12/1997 | Subbiah |
| 5,814,346 A | 9/1998 | Gamberini |
| 5,871,966 A | 2/1999 | Kofod et al. |
| 5,876,990 A | 3/1999 | Reddy et al. |
| 5,922,373 A | 7/1999 | Johnston |
| 5,935,623 A | 8/1999 | Alonso-Debolt |
| 6,045,834 A | 4/2000 | Howes et al. |
| 6,054,146 A | 4/2000 | Ballard et al. |
| 6,221,381 B1 | 4/2001 | Shelford et al. |
| 6,306,453 B1 | 10/2001 | Kuerzinger |
| 6,344,221 B1 | 2/2002 | Evans |
| 6,395,311 B2 | 5/2002 | Jia |
| 6,444,448 B1 | 9/2002 | Wheatcroft et al. |
| 6,468,964 B1 | 10/2002 | Rowe |
| 6,476,003 B1 | 11/2002 | Jordan et al. |
| 6,541,678 B2 | 4/2003 | Klein |
| 6,573,245 B1 | 6/2003 | Marciani |
| 6,623,866 B2 | 9/2003 | Migliorini et al. |
| 6,660,722 B2 | 12/2003 | Yvin |
| 7,527,816 B2 * | 5/2009 | Franz ................. A23K 10/37 426/285 |
| 7,598,061 B2 | 10/2009 | Forsberg et al. |
| 7,939,066 B2 | 5/2011 | Puntenney et al. |
| 8,142,798 B2 | 3/2012 | Forsberg et al. |
| 8,236,303 B2 | 8/2012 | Forsberg et al. |
| 8,431,133 B2 | 4/2013 | Forsberg et al. |
| 8,568,715 B2 | 10/2013 | Puntenney et al. |
| 8,663,644 B2 | 3/2014 | Forsberg et al. |
| 8,828,402 B2 | 9/2014 | Forsberg et al. |
| 8,834,868 B2 | 9/2014 | Forsberg et al. |
| 9,114,129 B2 | 8/2015 | Forsberg et al. |
| 9,173,926 B2 | 11/2015 | Forsberg et al. |
| 9,497,981 B2 | 11/2016 | Fahrenholz et al. |
| 10,555,964 B2 * | 2/2020 | Chapman ................ A61K 33/00 |
| 2002/0048573 A1 | 4/2002 | Klock et al. |
| 2003/0235565 A1 | 12/2003 | Cheung |
| 2004/0259015 A1 | 12/2004 | Tsubuko et al. |
| 2006/0115881 A1 | 6/2006 | Damude et al. |
| 2007/0253983 A1 | 11/2007 | Forsberg et al. |
| 2011/0195146 A1 | 8/2011 | Russi |
| 2011/0293736 A1 | 12/2011 | Cannock |
| 2012/0041081 A1 | 2/2012 | Hammond et al. |
| 2013/0196021 A1 | 8/2013 | Miller et al. |
| 2015/0209416 A1 | 7/2015 | Puntenney et al. |
| 2015/0250842 A1 | 9/2015 | Calabotta et al. |
| 2015/0374740 A1 | 12/2015 | Forsberg et al. |
| 2016/0129092 A1 | 5/2016 | Forsberg et al. |
| 2017/0072002 A1 | 3/2017 | Bafundo et al. |
| 2017/0202244 A1 | 7/2017 | Calabotta et al. |

FOREIGN PATENT DOCUMENTS

| | | |
|---|---|---|
| EP | 0721741 A1 | 7/1996 |
| EP | 1088483 A1 | 4/2001 |
| EP | 1129627 A1 | 9/2001 |
| EP | 2674397 A1 | 12/2013 |
| JP | 07184595 A | 7/1995 |
| WO | WO 95/30022 A1 | 11/1995 |
| WO | WO 97/02356 A1 | 1/1997 |
| WO | WO 2007/021262 | 2/2007 |

OTHER PUBLICATIONS

AOAC. Official Methods of Analysis of AOAC International. 16th Edition. vol. 1, Chapter 4, p. 4 (4.1.10). AOAC Official Method 942.05 Ash of Animal Feed. (1997).

Baumgard et al., "Ruminant Production and Metabolic Responses to Heat Stress," *Journal of Animal Science* 2012, 90:1855-1865.

Burton et al., "Immunity and Mastitis. Some New Ideas for an Old Disease," *Vet Clin. Food Anim.*, 19:1-45 (2003).

Burton, et al., "Gene expression signatures in neutrophils exposed to glucocorticoids: A new paradigm to help explain "neutrophil dysfunction" in parturient dairy cows," *Vet Immunol Immunopathol.*, 15:105(3-4):197-219 (2005).

Carroll et al., "Influence of Stress and Nutrition on Cattle Immunity," *Vet Clin Food Anim*, 23:105-149 (2007).

Chapman et al., "Effects of Omnigen AF on milk production and on lactation persistence in a commercial dairy setting," *Journal of Animal Science*, 83(1) Abstract T177 (Jul. 2005).

Derwent Publications Ltd., London, GB; XP002359382 & RU 2 115 421 C1 (Devichenskii V M) Jul. 20, 1998, abstract.

(56) References Cited

OTHER PUBLICATIONS

Derwent Publications Ltd., London, GB; XP002359383 & RU 2 093 162 C1 (AS SIBE BIOCHEM INT) Oct. 20, 1997, abstract.
Devegowda, Paper presented at African Lecture Tour, Mycotoxins in Feed, Novel Biotechnological Solutions, pp. 1-8 (Mar. 10-15, 1997).
Dhabhar, "Enhancing versus Suppressive Effects of Stress on Immune Function: Implications for Immunoprotection and Immunopathology," *Neuroimmunomodulation,* 16:300-317 (2009).
Examination Report dated Oct. 15, 2018, for related Australian Application No. 2017208321, 4 pp.
Galon, et al., "Gene profiling reveals unknown enhancing and suppressive actions of glucocorticoids on immune cells," *The FASEB Journal,* 16:61-71 (2002).
Hall et al., "Evaluation of OmniGen AF in heat-stressed Holstein cows in lactation," Abstract 458, *J. Anim. Sci.* vol. 91, E Suppl. 2/*J. Dairy Sci.* vol. 96, E-Suppl. 1, pp. 447-450, May 20, 2013.
Hall et al., "Evaluation of OmniGen AF in heat-stressed Holstein cows in lactation," Feb. 17, 2014, downloaded from http://dairy.ifas.ufl.edu/rns/2014/collier.pdf on Feb. 9, 2015, 12 pp.
Hall et al., "An evaluation of an immunomodulatory feed ingredient in heat-stressed lactating Holstein cows: Effects on hormonal, physiological, and production responses," *J. Dairy Sci* 2018, 101:7095-7105.
Healy, "Ingestion of soil by dairy cows," New Zealand Journal of Agriculture, 11(2):487-499 (1968).
International Search Report and Written Opinion dated Jan. 16, 2006 for PCT/US2005/028529, 9 pp.
International Search Report and Written Opinion dated Oct. 8, 2007 for PCT/US2007/066968, 14 pp.
International Search Report and Written Opinion dated Apr. 14, 2015 for PCT/US2015/015692, 9 pp.
Jensen et al., "The occurrence of fungi in bovine tissues in relation to portals of entry and environmental factors," *J. Comp. Path.,* 107:127-140 (1992).
Kessler et al., "Glucomannan-protein complexes from cell walls of yeast," *Journal of Biological Chemistry,* 234(9):2281-2285 (1959).
Label, Cenzone Tech, Inc., Microbond, circa 2000.
Leiva et al., "Supplementing an immunomodulatory feed ingredient to modulate thermoregulation, physiologic, and production response in lactating dairy cows under heat stress conditions," *J. Dairy Sci.* 100:4829-4838 (2017).
Lowry et al., "Purified β-Glucan as an Abiotic Feed Additive Up-Regulates the Innate Immune Response in Immature Chickens Against *Salmonella enterica* Serovar Enteritidis," *International Journal of Feed Microbiology* 98, 93(3):309-318 (2005).
Lyons, "Biotechnology in the Feed Industry," Proceedings of Alltech's Eleventh Annual Symposium, edited by TP Lyons and KA Jacques, Nottingham University Press, pp. 1-29 (1995).
Magnoli et al., "The mycoflora and toxicity of feedstuffs from a production plant in Cordoba, Argentina," *Mycotoxin Research,* 18(1):177-184 (2002).
Mahesh et al., "Ability of Aflatoxin Binders to Bind Aflatoxin in Contaminated Poultry Feeds and Liquid Media in vitro," poster presented at Twelfth Symposium on Biotechnology in the Feed Industry (Apr. 1996).
Mayland et al., "Soil ingestion by cattle grazing crested wheatgrass," *Journal of Range Management,* vol. 30(4), p. 264-265, Jul. 1977.
Mayer, "Cytokines and Immunoregulation," *Immunoregulation and Cytokines,* Immunology-Chapter Thirteen, pp. 1-5, updated Jul. 2010, downloaded from http://pathmicro.med.sc.edu/bowers/immreg-ver2.htm on Nov. 13, 2012.
McCausland et al., "Mycotic abortion in cattle," Australian Veterinary Journal, 64(5):129-132 (May 1987).
Mostl et al., "Hormones as indicators of stress," *Domestic Animal Endocrinology,* 23:67-74 (2002).
O'Connor, "Manage Heat Stress and Immunity in Dairy Cows with Nutritional Strategies," *Dairy Today: Healthline,* Jul. 8, 2013.
Ohsawa, "Clinical and pathological analysis of deep mycosis," *Kansenshogaku Zasshi,* 65(2):200-208 (Feb. 1991).

Omnigen AF Product Information at www.omnigenresearch.com/feed.php, Accessed Jan. 27, 2008.
Patil et al., "Immune response of calves to bentonite and alum adjuvanted combined vaccine . . . " *Indian Journal of Animal Sciences,* 74: 845-847 (Aug. 2004).
Pavelic, K et al., "Immunostimulatory effect of natural clinoptilotie as a possible mechanism of its antimetastatic ability," *J Cancer Res. Clin. Oncol.,* 128:37-44 (2002), 8 pp.
Phibro Animal Health Corporation, "Managing Heat Stress to Protect Dairy Cattle Immune Function and Productivity," May 13, 2014, 3 pp.
Phibro Animal Health Corporation, "Nutrition and Heat Stress," Jul. 1, 2013, 3 pp.
Prescott et al., "Fungal infections of the small and large intestine," J. Clin. Pathol., 45(9): 806-811 (Sep. 1992).
Prince Agri Products, Inc., "Proper Nutrition Plays Key Role to Help Protect Dairy Cattle against Heat Stress," *Hoards Dairyman,* Jul. 1, 2013.
Product Bulletin, Bill W. Perkins, Biotech Development Company, Inc., Dexter, Missouri, T-Bind pp. 1-20 (2000).
Product Bulletin Cenzone Tech, Inc., Microbond, The Proven Mycotoxin Adsorbent that Aids in the Binding and Diminishing the Adverse Effects of Mycotoxins, pp. 8-14 (Dec. 9, 2005).
Product Bulletin, CIENDAX S.A. Pronady 500, 100% yeast cell wall (*Saccharomyces cerevisiae*), pp. 1-4 (2000).
*Proposed Pretrial Order, Alltech, Inc.* v. *Cenzone Tech, Inc.,* U.S. District Court for the Southern District of California, Civil Action No. 06-CV0153 JM (RBBx), Jul. 31, 2007.
Puntenney et al., "Mycotic infections in livestock: recent insights and studies on etiology, diagnostics and prevention of hemorrhagic bowel syndrome," Proceedings of the 18th Southwest Nutrition and Management Conference, Phoenix, AZ (Feb. 20-21, 2003).
Rea, et al., "Glucocorticoids transform CD40-triggering of dendritic cells into an alternative activation pathway resulting in antigen-presenting cells that secrete IL-10," *Immunobiology,* 95(10):3162-3167 (2000).
Savage et al., "The Performance of Male Turkeys Fed a Starter Diet Containing a Mannan Oligosaccharide (Bio-Mos) from Day Old to Eight Weeks of Age," Proceedings of Alltech's Twelfth Annual Symposium, edited by TP Lyons and KA Jacques, Nottingham University Press, pp. 47-54 (1996).
Skibiel, et al., "Effect of OmniGen-AF supplementation to heat stressed cows during late gestation on blood parameters and immune cells of their calves," Joint Annual Meeting of ASAS-ADSA-CSAS-WSASAS (2016), abstract only, 2 pp.
Specification Sheet, Cenzone Tech, Inc., A.I.P. Co., Ltd., Microbond, The proven mycotoxin adsorbent pp. 1-8 (circa 2000).
Tangarone et al., "Purification and characterization of an endo-(1,3)-beta-D-glucanase from *Trichoderma longibrachiatum,*" Applied and Environmental Microbiology, 55(1):177-184 (1989).
Tao et al., "Effect of heat stress during the dry period on mammary gland development," *Journal of Dairy Science,* 94(12):5976-5986 (2011). 4 page Abstract only.
Tao et al., "Effect of heat stress during the dry period on mammary gland develpoment." *J Dairy Science,* vol. 94:12, p. 5976-5986 (2011).
U.S. Department of Health and Human Services Food and Drug Administration Center for Veterinary Medicine, Guidance for Industry, Dioxin in Anti-Caking Agent Used in Animal Feed and Feed Ingredients, Oct. 1999.
Vetvicka, V., "β-Glucans as Tmmunomodulators," *JANA,* 3(4):31-34 (2001).
Wang et al., "Identification of the mechanisms by which Omnigen-AF, a nutritional supplement, augments immune function in ruminant livestock," Proceedings, Western Section, American Society of Animal Sciences, 56:349-352 (2004).
Wang, et al., "Ability of a commercial feed additive to modulate expression of innate immunity in sheep immunosuppressed with dexamethasone," *Animal,* 1:945-951, doi: 10.1017/S1751731107000365 (2007).
Watson et al., "Stress and immune competence in feedlot cattle," *Recent Advances in Animal Nutrition in Australia,* 9:130-136 (Apr. 18-21, 1993).

(56) References Cited

OTHER PUBLICATIONS

Weber et al., "Pre-Translational Regulation of Neutrophil L-selectin in Glucocorticoid-Challenged Cattle," *Vet. Immunol. Immunopath.*, 83:213-240 (2001).

Werling et al., "Differential Production of Cytokines, Reactive Oxygen and Nitrogen by Bovine Macrophages and Dendritic Cells Stimulated with Toll-like Receptor Agonists," *Immunology*, 111:41-52 (2004).

White et al., "Haplotype Variation in Bovine Toll-like Receptor 4 and Computational Prediction of a Positively Selected Ligand-Binding Domain," *PNAS*, 100(18):10364-10369 (Sep. 2, 2003).

Whitney, M.H., et al. "Economic Evaluation of Nutritional Strategies that Affect Manure Volume, Nutrient Content, and Odor Emissions." Feb. 21, 2005, XP0552330177. Retrieved from the internet: URL:http://www.extension.umn.edu/-agriculture/swine/components/pubs/pub009.pdf.

Williams et al., "Effects of the inclusion of yeast culture (*Saccharomyces cerevisiae* plus growth medium) in the diet of dairy cows on milk yield and forage degradation and fermentation patterns in the rumen of steers," *Journal of Animal Science*, 69:3016-3026 (1991).

Colombo et al., "Supplementing an Immunomodulatory Feed Ingredient to Improve Thermoregulation and Performance of Finishing Beef Cattle Under Heat Stress Conditions," *Journal of Animal Science*, 2019, pp. 4085-4092.

Crook et al., "Influence of an Immune-Modulatory Feed Supplement on Performance and Immune Function of Beef Cows and Calves Preweaning," *Journal of Animal Science*, 2020, pp. 1-9.

Fabris et al., "Effect of Nutritional Immunomodulation and Heat Stress During the Dry Period on Subsequent Performance of Cows," *J. Dairy Sci.*, 2017, 100:6733-6742.

Gandra et al., "Influence of a Feed Additive Containing Vitamin $B_{12}$ and Yeast Extract on Milk Production and Body Temperature of Grazing Dairy Cows Under High Temperature-Humidity Index Environment," *Livestock Science*, 2019, 221:28-32.

McBride et al., "Response to Adrenocorticotropic Hormone or Corticotrophin-Releasing Hormone and Vasopressin in Lactating Cows Fed an Immunomodulatory Supplement Under Thermoneutral or Acute Heat Stress Conditions," *J. Dairy Sci.*, 2020, 103:6612-6626.

Pacheco et al., "Does Shading and Feed Additive (Omnigen-AF®) Improve Performance, Carcass Traits and Health of *Bos indicus* Feedlot Cattle Finished in a Tropical Environment?" *OmniGen Shade Final Report*, Oct. 2020, 47 pages.

Skibiel et al., "Effects of Feeding an Immunomodulatory Supplement to Heat-Stressed or Actively Cooled Cows During Late Gestation on Postnatal Immunity, Health, and Growth of Calves," *J. Dairy. Sci.*, 2017, 100:7659-7668.

\* cited by examiner a, b. Denotes differences (P<0.05) between treatment groups a, b, Denotes differences (P<0.05) between treatment groups at specific time points a, b. Denotes differences (P<0.05) between treatment groups at specific time points a,b Denotes differences (P<0.05) between treatment groups at specific time points

COMPOSITION AND METHOD FOR PROMOTING REDUCTION OF HEAT STRESS IN ANIMALS

CROSS-REFERENCE TO RELATED APPLICATIONS

This is a continuation of U.S. application Ser. No. 15/234,971, filed Aug. 11, 2016, issued as U.S. Pat. No. 10,555,964, which is a continuation of International Application No. PCT/US2015/015692, filed Feb. 12, 2015, which was published in English under PCT Article 21(2), which in turn claims the benefit of the earlier filing date of U.S. Provisional Application No. 62/000,986, filed May 20, 2014, and the benefit of the earlier filing date of U.S. Provisional Application No. 61/939,206, filed Feb. 12, 2014, each of which is incorporated by reference herein in its entirety.

FIELD

This disclosure relates to methods and compositions for promoting reduction of heat stress in animals.

BACKGROUND

Heat stress causes significant economic losses in animal industries, such as dairy industries. Production, reproduction and animal health are impaired by hyperthermia. Physiological and production responses are well documented, but not fully understood. During heat stress, respiration rates and body temperatures increase, and feed intake, milk yield, and reproduction decrease.

Milk synthesis decreases from reduced feed intake. There are additional losses in milk yield that are associated metabolic changes (Rhoads et al., 2009). Countering the production effects of heat stress in lactating dairy cows involves reduced maintain feed intake and controlling metabolic flux.

Immune function and health are also reduced with heat stress. The severity and occasion of disease are increased when immune and inflammatory responses are impaired. The rumen environment can be altered during thermal stress. Increased respiration rates can cause respiratory alkalosis, rumen acidosis and eventually metabolic acidosis. Oxidative stress can be increased with heat stress and can impair the heat shock response and increase cell damage and death.

SUMMARY

The object of the present disclosure is to provide a novel and previously unknown method for promoting reduction of heat stress in animals. Also disclosed herein is a composition suitable for administering to animals in order to substantially prevent and/or promote reduction of heat stress in animals. The disclosed composition and method for preventing and/or promoting reduction of heat stress may be applied to any animal species susceptible to heat stress, such as mammals, avians, or aquatic animal species. In some embodiments, the animals treated herein can be an animal raised for human consumption, such as livestock (e.g., feed or dairy cattle) or pigs, or avians, such as domestic fowl (e.g., chicken, turkey, goose, duck, cornish game hen, quail, pheasant, guineafowl, ostrich, emu, swan, or pigeon), or fish (e.g., salmon, trout and the like). In other embodiments, the animal can be a domestic animal, such as a dog, cat, fish, or rabbit. In some other embodiments, the animal can be a ruminant species, such as a sheep, goat, cow, deer, bison, buffalo, or llama. In yet other embodiments, the animal can be an ungulate, such as a horse, donkey, or pig.

Disclosed herein are embodiments of a method for promoting heat stress reduction in an animal, such as a mammal or avian species by administering to the mammal or avian species a composition comprising glucan, silica, mineral clay and mannan. In some embodiments the composition comprises between 15% and 40% silica, between 50% and 81% mineral clay, between 1.0% and 5.0% β-glucans, and between 1% and 8.0% mannan. In a particular embodiment the composition consists essentially of β-glucans, β-1,3 (4)-endoglucanohydrolase, diatomaceous earth, a mineral clay, and glucomannan.

In any or all of the above embodiments, the composition can be administered prophylactically, or when the animal has or is at risk of developing heat stress. Heat stress may occur when the animal is exposed to a temperature humidity index of 68 or greater, 75 or greater, or ≥79.

In any or all of the above embodiments, heat stress may be evidenced by a heat stress indicator. Heat stress indicators include, but are not limited to, feed intake, water consumption, respiration rate, rectal temperature, milk yield, milk fat, milk protein, or any combination thereof. In some embodiments the composition is administered prior to the animal experiencing heat stress while the animal is experiencing heat stress, and/or after the animal experiences heat stress. In any or all of the above embodiments, the animal may be immunosuppressed prior to administration of the composition, for example as a result of heat stress.

In any or all of the above embodiments, the composition may be administered at set intervals to the animal for an effective period of time to promote reduction of heat stress. The set interval can be daily, or it can be more or less frequently than that. In some embodiments the effective period of time is from 0 days to 200 days, from 1 day to 200 days, from 1 day to 90 days, from 1 day to 60 days, from 1 day to 45 days, from 1 day to 30 days, from 3 days to 21 days, at least 1 day, at least 3 days, at least 7 days, at least 30 days, at least 60 days, or at least 90 days.

In any or all of the above embodiments, the amount administered to the animal can range from 1 mg/kg body weight per day to 20 g/kg body weight per day. In any or all of the above embodiments, the composition may be administered by mixing the composition with the animal's feed in an amount ranging from 0.1 to 20 kg per ton of feed and providing the composition mixed with the feed to the animal. In some embodiments, the animal is a bovine and the amount administered to that animal can range from 0.5 grams to 100 grams daily.

In any or all of the above embodiments, an amount of the composition administered to the animal may be increased if the temperature humidity index is expected to increase or decreased if the temperature humidity index is expected to decrease.

In any or all of the above embodiments, the animal may be administered an amount of the composition effective to alter a heat stress indicator compared to an animal that has not been administered the composition. In some embodiments, the method further includes measuring the heat stress indicator, and selecting an amount of the composition administered to the animal based at least in part on the measurement of the heat stress indicator.

In particular embodiments the animal is a cow, such as, for example, a dairy cow. Dairy cows may be administered the composition before lactation. This can be from 90 days prior to lactation onset to 1 day prior to lactation onset, preferably from 45 days prior to lactation onset to 10 days prior to lactation onset. The composition may be administered daily prior to lactation onset. In any or all of the above embodiments, the dairy cow may be fed the composition for a period of time to increase milk production and/or reduce milk fat relative to dairy cattle not fed the composition.

The animal that is administered the composition may have reduced water intake relative to animals not fed the composition. The animal also may have a reduced respiration rate relative to animals not fed the composition. In other embodiments, the animal may have a reduced rectal temperature relative to animal not fed the composition. In particular disclosed embodiments, the animal may exhibit increased food intake relative to animal not fed the composition. Also, the animal may exhibit decreased respiratory alkalosis, rumen acidosis, metabolic acidosis, and any and all combinations thereof, relative to animals not fed the composition. In other embodiments, the animal may have decreased serum cortisol levels relative to animals not fed the composition.

In any or all of the above embodiments, the method may further comprise administering to the mammal or avian species a therapeutic process and/or a therapeutic agent suitable for treating heat stress. Exemplary therapeutic processes and agents include, but are not limited to, provision of shade to the animal, use of a water sprinkler to externally administer water to the animal, use of a fan to provide air movement, addition of bypass fats to feed for the animal, meloxicam, a corticosteroid, a composition comprising one or more electrolytes, an alkalinizing agent, a direct-fed microbial, or a combination thereof.

In any or all of the above embodiments, the method may include administering a first amount of the composition to a group of animals that have or are at risk of developing heat-induced stress for a first period of time, measuring a heat stress indicator of at least one animal of the group of animals, and administering an adjusted amount of the composition to the group of animals for a subsequent period of tie, wherein the adjusted amount is based at least in part on the measurement of the heat stress indicator.

In any or all of the above embodiments, the method may include evaluating at least one heat stress indicator of individual animals in a group of animals, determining whether one or more of the individual animals are experiencing heat stress, and administering the composition to the one or more individual animals that are experiencing heat stress.

An exemplary embodiment comprises selecting a dairy cow that has or is at risk of developing heat induced stress and administering to the dairy cow before, during, and/or after lactation a composition comprising glucan, silica, mineral clay, mannan, and optionally an endoglucanohydrolase, wherein the composition is administered at set intervals for an effective period of time sufficient to (1) increase milk production relative to dairy cattle not fed the composition, (2) lower milk fat relative to dairy cattle not fed the composition, (3) reduce water intake relative to dairy cattle not fed the composition, (4) reduce respiration rate relative to dairy cattle not fed the composition, (5) reduce rectal temperature relative to dairy cattle not fed the composition, (6) increase food intake relative to dairy cattle not fed the composition, (7) decrease respiratory alkalosis, rumen acidosis, and/or metabolic acidosis relative to dairy cattle not fed the composition, (8) decrease serum cortisol levels relative to dairy cattle not fed the composition, or (9) any and all combinations thereof. The method may further comprise administering to the dairy cow a therapeutic agent suitable for treating heat stress.

DETAILED DESCRIPTION

I. Definitions

Figure 1:
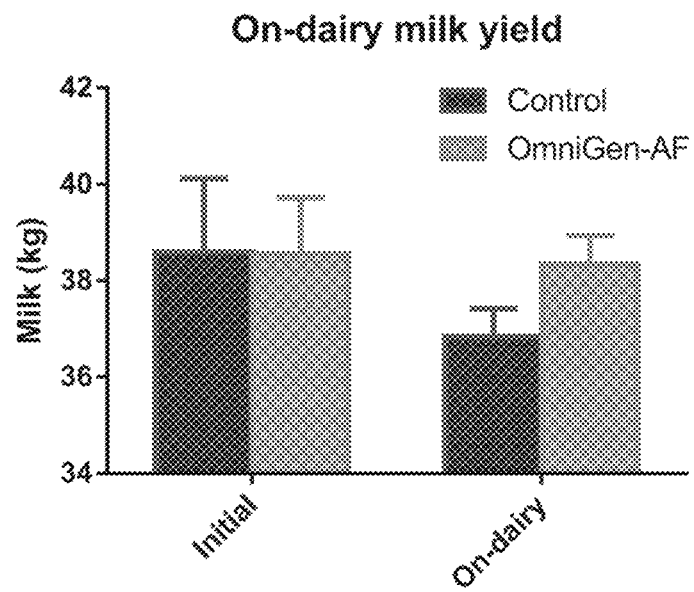
FIG. 1 is a bar chart illustrating on-dairy milk yield (kg) by cows that are administered the disclosed composition and those that are not, including both initial and on-dairy conditions.

The following explanations of terms and abbreviations are provided to better describe the present disclosure and to guide those of ordinary skill in the art in the practice of the present disclosure. As used herein, "comprising" means "including" and the singular forms "a" or "an" or "the" include plural references unless the context clearly dictates otherwise. The term "or" refers to a single element of stated alternative elements or a combination of two or more elements, unless the context clearly indicates otherwise.

Unless explained otherwise, all technical and scientific terms used herein have the same meaning as commonly understood to one of ordinary skill in the art to which this disclosure belongs. Although methods and materials similar or equivalent to those described herein can be used in the practice or testing of the present disclosure, suitable methods and materials are described below. The materials, methods, and examples are illustrative only and not intended to be limiting. Other features of the disclosure are apparent from the following detailed description and the claims.

Unless otherwise indicated, all numbers expressing quantities of components, molecular weights, percentages, temperatures, times, and so forth, as used in the specification or claims are to be understood as being modified by the term "about." Accordingly, unless otherwise indicated, implicitly or explicitly, the numerical parameters set forth are approximations that may depend on the desired properties sought and/or limits of detection under standard test conditions/methods. When directly and explicitly distinguishing embodiments from discussed prior art, the embodiment numbers are not approximates unless the word "about" is recited.

Animal: This term includes species that are produced for human consumption or that are domesticated animals. Exemplary species of such animals are provided herein.

Administering: Administration by any route to the subject. As used herein, administration typically refers to oral administration.

Mannans: A class of polysaccharides including the sugar mannose. The mannan family includes pure mannans (i.e., the polymer backbone consists of mannose monomers), glucomannans (the polymer backbone comprises mannose and glucose), and galactomannans (mannans or glucomannans in which single galactose residues are linked to the polymer backbone). Mannans are found in cell walls of some plant species and yeasts.

Mineral Clay: The term "mineral clay" refers to hydrous aluminum silicates. Mineral clays usually include minor amounts of impurities, such as potassium, sodium, calcium, magnesium, and/or iron. Mineral clays typically have a two-layer sheet structure including tetrahedral silicate sheets and octahedral hydroxide sheets or a three-layer structure including a hydroxide sheet between two silicate sheets.

Therapeutic agent: An agent that is capable of providing a therapeutic effect, e.g., preventing a disorder, inhibiting a disorder, such as by arresting the development of the disorder or its clinical symptoms, or relieving a disorder by causing regression of the disorder or its clinical symptoms.

Therapeutically effective amount: A quantity or concentration of a specified compound or composition sufficient to achieve a desired effect in a subject being treated for a disorder. The therapeutically effective amount may depend at least in part on the species of animal being treated, the size of the animal, and/or the severity of the disorder.

Additional disclosure is found in U.S. patent application Ser. No. 13/566,433, U.S. patent application Ser. No. 13/872,935, U.S. Patent Publication No. 2013/0017211, U.S. Patent Publication No. 2012/0156248, U.S. Patent Publication No. 2007/0253983, U.S. Patent Publication No. 2007/0202092, U.S. Patent Publication No. 20070238120, U.S. Patent Publication No. 2006/0239992, U.S. Patent Publication No. 2005/0220846, U.S. Patent Publication No. 2005/0180964, and Australian Patent Application No. 2011201420, all of which are incorporated herein by reference.

II. Composition

The present disclosure is based on the novel discovery that a combination of glucan, silica, mineral clay, mannans can effectively prevent or reduce heat stress in animals. Embodiments of the disclosed composition comprise one or more components as disclosed herein. The composition typically comprises glucan (e.g., β-1,3 (4)glucan), silica, mineral clay and mannans. In some embodiments, the composition further comprises an endoglucanohydrolase, such as β-1,3 (4)-endoglucanohydrolase. Suitable sources of silica include, but are not limited to, sand, quartz, diatomaceous earth, and synthetic silica. In certain embodiments, the mannans comprise glucomannan.

The components of the composition are prepared by methods commonly known in the art and can be obtained from commercial sources. At least some components of the composition (e.g., silica, mineral clay) also may be present in the environment. β-1,3 (4)-endoglucanohydrolase may be produced from submerged fermentation of a strain of *Trichoderma longibrachiatum*. Diatomaceous earth is available as a commercially-available acid-washed, product with 95% silica ($SiO_2$) and with its remaining components not assayed but consisting primarily of ash (minerals) as defined by the Association of Analytical Chemists (AOAC, 2002). The mineral clays (e.g., aluminosilicates) used in this composition may be any of a variety of commercially-available clays including, but not limited to, montmorillonite clay, bentonite and zeolite. Glucan and mannans can be obtained from plant cell walls, yeast (e.g., *Saccharomyces cerevisiae*, *Candida utilis*), certain fungi (e.g., mushrooms), and bacteria.

In one embodiment, the composition includes 1-40 wt % silica, 1-25 wt % glucan and mannans, and 40-92 wt % mineral clay. In another embodiment, the composition comprises 5-40 wt % silica, 2-15 wt % glucan and mannans, and 40-80 wt % mineral clay. In another embodiment, the composition comprises 20-40 wt % silica, 4-10 wt % glucan and mannans, and 50-70 wt % mineral clay. In another embodiment, the composition comprises 15-40 wt % silica, 1-15 wt % glucans, 0-10 wt % mannans, and 50-81 wt % mineral clay. In another embodiment, the composition comprises 15-40 wt % silica, 1.0-5.0 wt % glucans, 1.0-8.0 wt % mannans, and 50-81 wt % mineral clay. In another embodiment, the composition comprises 20-30 wt % silica, 1.0-3.5 wt % glucans, 1.0-6.0 wt % mannans, and 60-75 wt % mineral clay.

In some embodiments, β-glucans and mannans are obtained from yeast cell wall extract, and Composition I comprises 1-40 wt % silica, 1-30 wt % yeast cell wall extract, 40-92 wt % mineral clay. In one embodiment, Composition I comprises 10-40 wt % silica, 5-20 wt % yeast cell wall extract, and 40-80 wt % mineral clay. In another embodiment, Composition I comprises 15-30 wt % silica, 5-15 wt % yeast cell wall extract, and 55-70 wt % mineral clay.

In any of the above embodiments, the composition may further comprise an endoglucanohydrolase, such as β-1,3 (4)-endoglucanohydrolase. The composition may include from at least 0.05 wt % endoglucanohydrolase to 5 wt % endoglucanohydrolase, such as from 0.05-3 wt % β-1,3 (4)-endoglucanohydrolase. In one embodiment, Composition I consists essentially of 0.1-3 wt % β-1,3 (4)-endoglucanohydrolase, 20-40 wt % silica, 2-20 wt % glucan and mannans, and 50-70 wt % mineral clay. In another embodiment, the composition consists essentially of 0.2-3 wt %, β-1,3 (4)-endoglucanohydrolase, 20-40 wt % silica, 4-10 wt % glucan and mannans, and 50-70 wt % mineral clay. In any of the above embodiments, the silica may be provided by diatomaceous earth. In any of the above embodiments, the glucans may be β-glucans. In some embodiments, the β-glucans can be obtained from yeast, or other materials, such as fungi, algae, or the like. In any of the above embodiments, the mannans may comprise glucomannan.

The glucan and mannans (or yeast cell wall extract) can be prepared by a method commonly known in the art. In an independent embodiment, it can be a commercial source of β-1,3 (4) glucan and glucomannan derived from primary inactivated yeast (*Saccharomyces cerevisiae*) with the following chemical composition:

Moisture 3.5-6.5%
Proteins 1-6%
Fats 0-0.5%
Phosphorus 0-0.2%
Mannans 9-20%
β-1, 3-(4) glucan 9-18%
Ash 75-85%; and in some embodiments, the composition can further comprise Dry matter 97-98%.

In another independent embodiment, the composition can comprise:

Moisture 2-3%
Dry matter 97-98%
Proteins 14-17%
Fats 20-22%
Phosphorus 1-2%
Mannans 22-24%
β-1, 3-(4) glucan 24-26%
Ash 3-5%.

The mineral clays (aluminosilicates) used in this composition may be fulfilled by any of a variety of commercially-available clays including, but not limited to, montmorillonite clay, bentonite and zeolite.

In an independent embodiment of the composition, silica, glucan and mannans, and mineral clay are combined at 1-40%, 1-25% and 40-92%, respectively. In an independent embodiment of the composition, β-1,3 (4)-endoglucanohydrolase, diatomaceous earth, yeast cell wall extract and mineral clay are combined at 0.05-3%, 1-40%, 1-20% and 40-92%, respectively. In an independent composition, β-1,3 (4)-endoglucanohydrolase, diatomaceous earth, yeast cell wall extract and mineral clay are combined at 0.1-3%, 5-40%, 2-10% and 40-80%, respectively. In another independent embodiment of the composition, β-1,3 (4)-endoglucanohydrolase, diatomaceous earth, yeast cell wall extract and mineral clay are combined at 0.2-3%, 30-40%, 4-6% and 50-65%, respectively.

In some embodiments, the composition includes additional components. Additional components may be used for any desired purpose, such as a substantially biologically inert material added, for example, as a filler, or to provide a desired beneficial effect. For example, the composition may include a carbonate (including a metal carbonate such as calcium carbonate), kelp, a vitamin (such as a niacin supplement or vitamin B-12 supplement), biotin, d-calcium pantothenate, choline chloride, thiamine mononitrate, pyridoxine hydrochloride, menadione dimethylpyrimidinol bisulfite, riboflavin-5-phosphate, folic acid, soybean oil, calcium aluminosilicate, rice hulls, mineral oil, or any combination thereof.

The composition may be formulated in any suitable form, including a powder, a granule, a pellet, a solution, or a suspension. In one embodiment, the composition can be a dry, free-flowing powder suitable for direct inclusion into a commercially-available feed, food product or as a supplement to a total mixed ration or diet. The powder may be mixed with either solid or liquid feed or with water. In another embodiment, the composition can be formed into pellets.

In one embodiment, when incorporated directly into feeds, the composition may be added in amounts ranging from 0.1 to 100 kg per ton, such as from 0.1 to 20 kg per ton (2000 pounds) of feed. In some embodiments, the composition can be added to animal feedstuffs or to food in amounts from 0.1 kg to 50 kg per ton, from 0.1 to 20 kg per ton, or from 0.5 kg to 10 kg per ton of feed. In certain embodiments, the composition may be added to feeds in amounts ranging from 1 to 5 kg per ton of feed.

When expressed as a percentage of dry matter of feed, the composition may be added to animal feedstuffs or to foods in amounts ranging from 0.01 to 2.5% by weight, such as from 0.0125% to 2% by weight. In one embodiment, the composition can be added to animal feedstuffs or to food in amounts from 0.05 to 1.5% by weight, such as from 0.06% to 1% by weight. In another embodiment, the composition can be added in amounts from 0.1 to 0.7% by weight, such as from 0.125% to 0.5% by weight of feed.

Alternatively, the composition may be fed directly to the animal as a supplement in amounts of from 0.01 gram to 20 gram per kilogram of live body weight per day, such as from 0.01 gram to 10 gram per kilogram, 0.01 gram to 5 gram, 0.01 gram to 1 gram, 0.015 gram to 1 gram, or 0.02 gram to 0.4 gram per kilogram of live body weight per day. In some embodiments, the composition may be provided for use with many species in amounts of from 0.05 grams to 0.20 grams per kilogram of live body weight per day.

Additionally, the composition may be fed to mammalian animals or avian species as a supplement (in combination with other feed, or alone) in amounts ranging from 10 grams per head per day to 70 grams per head per day, such as from 40 grams per head per day to 70 grams per head per day, from 45 grams per head per day to 70 grams per head per day, or from 50 grams per head per day to 70 grams per head per day. In exemplary embodiments, the composition can be provided to bovines in an amount ranging from 50 grams per head per day to 60 grams per head per day, such as 56 grams per head per day.

The physical form of the composition can be a dry, free-flowing powder which is suitable for direct inclusion into a feed, food product or as a supplement to a total mixed ration or diet.

Alternatively, the composition contained in the present composition may be fed directly to mammalian or avian species as a supplement in amounts 0.016 grams/kg to 0.37 grams/kg of live body weight per day. In an independent embodiment, the composition may be provided to mammalian and avian species in amounts of 0.10 grams/kg to 0.20 grams/kg of body weight per day.

In particular disclosed embodiments, the composition may be administered to the mammal or avian species using a carrier. The carrier may be any carrier known to a person of ordinary skill in the art as being suitable for combining with a feed composition, such as molasses. In some embodiments, the composition includes additional ingredients. For example, the composition includes calcium carbonate, dried kelp, niacin supplement, biotin, d-calcium pantothenate, vitamin B-12 supplement, choline chloride, thiamine mononitrate, pyridoxine hydrochloride, silicon dioxide, riboflavin-5-phosphate, folic acid, soybean oil, or any combination thereof.

One of skill in the art can appreciate that the amount of the claimed composition fed can vary depending upon the animal species, size of the animal and type of the feedstuff to which the claimed composition is added.

III. Reducing Heat Stress

In particular disclosed embodiments, the composition disclosed herein may be used to prevent and/or promote reduction of heat stress in animals. Heat stress can impair production, reproduction, and animal health. For example, heat stress can lead to increased respiratory rate, increased body temperature, increased fluid intake, decreased feed intake, decreased weight gain, decreased milk yield, decreased reproduction, respiratory alkalosis, ruminal alkalosis, metabolic acidosis, increased oxidative stress, decreased immune function, and/or increased cell damage and death. Accordingly, any of the foregoing factors may be assessed as heat stress indicators. In some embodiments, the heat stress indicator is feed intake, water consumption, respiration rate, rectal temperature, milk yield, milk fat, milk protein, an immune biomarker, or any combination thereof. In certain embodiments, the heat stress indicator is feed intake, water consumption, respiration rate, rectal temperature, milk yield, milk fat, milk protein, or any combination thereof.

In some embodiments, heat stress conditions occur when a temperature humidity index (THI) is greater than 68, such as greater than 75, ≥79 (regarded as a dangerous level), or ≥84 (regarding as an emergency level). In another embodiment, heat stress conditions occur when the heat index, commonly reported by the media for humans, is above 100, such as above 110, above 115, or above 120.

The composition may be administered to an animal that is susceptible to heat stress or that suffers from heat stress. In one embodiment, the composition is administered to the animal when the temperature humidity index is, or is expected to be, greater than 68. The composition may be administered to the animal at set intervals. For example, the composition may be administered to the animal on a daily basis. In some embodiments, a daily amount of the composition is divided and administered to the animal at two or more feedings.

In some embodiments, the animal can be an animal raised for human consumption including, but are not limited to mammals, such as livestock (e.g., feed or dairy cattle) or pigs; avians, such as domestic fowl (e.g., chicken, turkey, goose, duck, cornish game hen, quail, pheasant, guineafowl, ostrich, emu, swan, or pigeon); or fish (e.g., salmon, trout and the like). In other embodiments, the animal can be a domestic animal, such as a dog, cat, fish, or rabbit. In some other embodiments, the animal can be a ruminant species, such as a sheep, goat, cow, deer, bison, buffalo, or llama. In yet other embodiments, the animal can be an ungulate, such as a horse, donkey, or pig.

The disclosed method and composition can be used to promote reduction of heat stress in any mammalian (including human), avian, or aquatic species. In a particular embodiment, the compositions are administered to livestock animals, including both ruminants (e.g., cattle, sheep, goats, cows, deer, bison, buffalo) and non-ruminants (e.g., pigs, horses, sows).

The composition disclosed herein may be administered in an amount effective to promote reduction of heat stress in animals, such as dairy cows, particularly lactating dairy cows. The composition may be administered pre- or post-calving for a suitable number of days. The composition also may be administered prior to lactation or after lactation. For example, the composition may be administered to the animal for a period of from 1 day prior to lactation onset to 100 days prior to lactation onset. In other disclosed embodiments, the composition may be administered to the animal for 40 days to 100 days post calving, or for 45 days to 95 days post calving, or for 50 days to 90 days post calving.

In some embodiments, a dairy cow is fed the composition for a period of time to increase milk production relative to dairy cattle not fed the composition. In particular embodiments, the dairy cow has lower milk fat relative to dairy cattle not fed the composition. In one embodiment, the dairy cow had reduced water intake relative to dairy cattle not fed the composition. In another embodiment, the dairy cow had a reduced respiration rate relative to dairy cattle not fed the composition. In yet another embodiment, the dairy cow had a reduced rectal temperature relative to dairy cattle not fed the composition. The dairy cow may have increased food intake relative to dairy cattle not fed the composition. In particular disclosed embodiments, the dairy cow may have decreased respiratory alkalosis, rumen acidosis, metabolic acidosis, and any and all combinations thereof, relative to dairy cattle not fed the composition. In another embodiment, the dairy cow has decreased serum cortisol levels relative to dairy cattle not fed the composition.

In additional disclosed embodiments, the composition may be administered prophylactically. In certain embodiments, the composition may be administered prophylactically and continuously. For example, the animal may be administered the composition every day for a certain period of time prior to and during lactation.

The disclosed composition may be formulated for administration to animals in order to prevent and/or promote reduction of heat stress. In particular disclosed embodiments, the effective amount of the composition administered can be affirmatively chosen based on the ability of that effective amount to promote heat stress reduction in an animal based on particular factors disclosed herein. In particular disclosed embodiments, the effective amount may be determined by administering a particular first dose to the animal, monitoring the animal during heat stress, and then adjusting the dose in order to determine an effective amount of a second dose that will ameliorate, or further ameliorate the heat stress of the animal.

In one embodiment, the composition is administered to a group of animals that have or are at risk of developing heat stress. The composition may be administered to the group of animals in a first amount for a first period of time. Subsequently a heat stress indicator of at least one animal in the group of animals is measured. Based at least in part on the heat stress indicator measurement, the amount of composition administered to the group of animals for a subsequent period of time may be adjusted. For example, the amount may be increased if the heat stress indicator measurement indicates that the animals are stressed. Alternatively, the amount may be decreased if the heat stress indicator measurement indicates that the animals are not stressed or have relatively little heat stress.

In another embodiment, individual animals in a group of animals are evaluated for heat stress. Heat stress can be evaluated, for example, by measuring a level of one or more heat stress indicators. Based at least on the measurement, a determination is made whether one or more of the individual animals is experiencing heat stress. Individual animals in the group that are experiencing heat stress may be selected to receive the composition for a period of time effective to promote reduction of heat stress.

In particular disclosed embodiments, the composition may be administered with a molasses carrier once or multiple times a day (e.g., from two to five times per day). The composition may be mixed into the total mixed ration of feed that can be provided to the mammal or avian species, such as in the top one-fourth, top one-third, or top one-half of the total mixed ration.

In some embodiments, the animal is further administered a therapeutic process and/or a therapeutic agent suitable for treating stress. Exemplary therapeutic processes and agents include, but are not limited to, provision of shade to the animal, use of water sprinklers to externally administer water to the animal, use of a fan to provide air movement, addition of high-fat feeds or bypass fats, meloxicam, corticosteroids (isoflupredone, fludrocortisone, triamcinolone, dexamethasone, betamethasone, flumethasone, methylprednisolone acetate, methylprednisolone sodium succinate), oral electrolytes (e.g., sodium, glucose, glycine, potassium, chloride) alkalinizing agents (e.g., bicarbonate, acetate, and/or citrate salts), direct-fed microbials, and combinations thereof.

The ability of the composition to reduce and/or prevent heat stress may be determined by comparing heat stress indicators with animals that are not administered the composition. In particular disclosed embodiments, heat stress indicators may be used to determine the effect of the composition on heat stress. Suitable heat stress indicators/factors include, but are not limited to, feed intake, milk yield, milk fat, milk protein, water consumption, respiration rates, rectal temperatures, and combinations thereof.

In particular disclosed embodiments, animals that are administered the composition will have a higher feed intake during heat stress compared to animals that are not administered the composition. The feed intake during heat stress may increase from 2 kg to 10 kg (or from 2 kg to 8 kg, or from 2 kg to 6 kg, or 2 kg to 4 kg) compared to the feed intake of an animal of the same species has not been administered the composition. In exemplary embodiments, a bovine that is administered the composition will have feed intake of 3 kg higher than a bovine who has not been administered the composition.

The milk yield also may be maintained or increased (as compared to yields from animals that are not administered the composition) during heat stress by administering the composition. For example, the milk yield may increase by 1 kg, 2 kg, 3 kg, 4 kg, up to 10 kg using the disclosed composition. In particular disclosed embodiments, animals that are provided the composition will produce milk having lower milk fat and/or milk protein (in terms of percentage). For example, milk fat may be reduced from 0.2% to 1%, or from 0.2% to 0.8%, or from 0.2% to 0.6%, with exemplary embodiments including a 0.4% reduction. In one embodiment, a dairy cow fed the composition produces a milk fat percentage of 3.8%, whereas dairy cattle not fed the composition have a milk fat percentage of 4.2%.

Water consumption, respiration rates, and serum cortisol levels also are lowered by administering the disclosed composition, with some embodiments exhibiting from 4 to 10 fewer respirations per minute. Another factor indicating that the disclosed composition is capable of reducing heat stress is rectal temperature, which typically may be lowered by 0.10° C. to 0.3° C., in comparison to the rectal temperatures taken from animals that are not administered the composition. Additionally, animals that have been administered the disclosed composition may have decreased respiratory alkalosis, rumen acidosis, metabolic acidosis, and combinations thereof in comparison to animals that were not administered the composition.

IV. Examples

Example 1

A total of 60 cows on a commercial dairy in Arizona were balanced for DIM, parity and milk production and assigned to 1 of 2 treatment groups fed the disclosed composition (OmniGen-AF® [OG] comprising between 15% and 40% silica, between 50% and 81% mineral clay, between 1.0% and 5.0% β-glucans, between 0.05% and 3.0% β-1,3 (4)-endoglucanohydrolase and between 1% and 8.0% mannan, 30 cows) or control (CON, 30 cows) diets for 52 d post calving. At 52 d of lactation cows were randomly selected (n=12) from both groups (6 OG and 6 CON) and housed in environmentally controlled modules for 21 d. The OG was top-dressed 2×/d with molasses as the carrier and the CON cows received the molasses carrier 2×/d. Both were mixed into the top one-third of the TMR (total mixed ration). During the environmental room phase of the study cows fed OG had higher feed intake than CON during heat stress (HS) (46.8 kg vs. 42.9 kg, P<0.0001) and no difference during thermoneutral (TN). A temperature-humidity index (THI) threshold of 68 or greater was used to achieve HS. Feeding OG maintained a numerical 1 kg milk yield advantage compared with CON (30.3 kg vs. 31.4 kg, P=0.26) during HS but not during TN. Cows fed OG had lower milk fat (%) (4.2% vs. 3.8%, P=0.02) and milk protein (%) (P=0.04). There was no difference in 3.5% FCM between treatments. Water consumption was lower (12.4l/d in OG treated cows, P<0.01) than control cows. Respiration rates were lower in treated cows at 1400 h and 1700 h (4.7 and 8.4 less respirations/min, P=0.05, <0.001) and rectal temperatures were also lower (0.15° C. and 0.25° C. lower that CON, P=0.05, <0.001) in treated cows. Feeding OG reduced physiological responses to heat stress in lactating dairy cows.

Example 2

A total of 30 cows on a commercial dairy in Arizona were balanced for DIM, parity and milk production and assigned to 1 of 2 treatment groups fed the disclosed composition (OmniGen-AF® [OG] comprising between 15% and 40% silica, between 50% and 81% mineral clay, between 1.0% and 5.0% β-glucans, between 0.05% and 3.0% β-1,3 (4)-endoglucanohydrolase and between 1% and 8.0% mannan, 15 cows) or control (CON, 15 cows) diets for 90 d post calving. At 90 d of lactation, cows were randomly selected (n=12) from both groups (6 OG and 6 CON) and housed in environmentally controlled modules for 21 d at the University of Arizona. The OG was top-dressed 2×/d with molasses as the carrier. The CON cows received the molasses carrier 2×/d. Both were mixed into the top one-third of the TMR. During the environmental room phase of the study, cows fed OG had higher feed intake than CON during heat stress (HS) (46.8 kg vs. 42.9 kg, P<0.0001) and no difference during thermoneutral (TN). A temperature-humidity index (THI) threshold of 68 or greater was used to achieve HS. Feeding OG maintained a numerical 1 kg milk yield advantage compared with CON (30.3 kg vs. 31.4 kg, P=0.26) during HS but not during TN. Cows fed OG had lower milk fat (%) (4.2% vs. 3.8%, P=0.02) and milk protein (%) (P=0.04). There was no difference in 3.5% FCM between treatments. Water consumption was lower (12.4l/d in OG treated cows, P<0.01) than control cows. Respiration rates were lower in treated cows at 1400 h and 1700 h (4.7 and 8.4 less respirations/min, P=0.05, <0.001) and rectal temperatures were also lower (0.15° C. and 0.25° C. lower that CON, P=0.05, <0.001) in treated cows. Feeding OG reduced physiological responses to heat stress in lactating dairy cows.

Experimental Design:

The study consisted of two phases; 1) the commercial dairy, and 2) the controlled environmental chambers. During the commercial dairy phase, multiparous lactating Holstein cows (n=30) were balanced by DIM, milk production and parity (91±5.9 DIM, 36.2±2.5 kg/d, and 3.1±1.4). Cows were separated into one of two groups. The control group received the base TMR with no supplement. The treatment group was fed the base diet plus 56 g/head/day of OmniGen-AF® composition (OG) mixed into the TMR. Daily milk production was measured. The dairy phase lasted for 45 days. The dairy portion was used to meet the manufacture's recommended 45 d feeding for OG composition to function.

After the on-dairy portion was complete, 12 cows (6 control and 6 treatment) were housed in the environmentally controlled rooms at the Agricultural Research Center (ARC). Cows continued the ARC portion in the same treatment groups from the on-dairy portion.

The ARC portion lasted for 21 days. Cows were subjected to 7 days of TN conditions, 10 days of HS, and 4 days of recovery (TN). The diurnal cycle during thermoneutral (TN) and recovery maintained a temperature humidity index (THI)<68. During HS, the THI was greater than 68 for 16 hours/day. Temperatures mimicked ambient temperatures at a southwest United States dairy during summer heat and TN conditions. Fresh feed was provided twice daily and cows were individually fed. Control animals received base TMR, and OG cows received 56 g/head per day, split between two meals. Feed intake, milk production, and milk composition were measured daily. Rectal temperatures and respiration rates were recorded 3×/d (600, 1400, and 1800 h). Blood samples were taken by venipuncture from the tail (coccygeal) vein on days 7 (TN), 8 (HS), 10 (HS), 17 (HS) and 18 (TN) during the ARC segment. Samples were collected 6 times per day (0400, 0800, 1200, 1600, 2000, and 2400 h) on days 7, 8, 17, and 18, and once per day on day 14 (0800 h). Blood was collected in Vacutainer (BD Vacutainer, Franklin Lakes, N.J.) tubes containing sodium heparin for plasma and in sterile blank tubes for serum.

Statistical analyses were performed using the PROC MIXED procedure (version 9.3, SAS Institute, Cary, N.C.). Cow was the experimental unit (ARC portion). Data is presented in least square means with significance declared with a P-value ≤0.05. (See Table 1, below).

There were no initial differences in milk yield (control=38.6 kg/day and treatment=38.6 kg/day) at the start of the on-dairy phase of the study. There was a numerical advantage to feeding OG (FIG. 1) of 1.5 kg of milk/day, but this was not significant (control=36.8 kg/day and treatment=38.3 kg/day).

Figure 2:
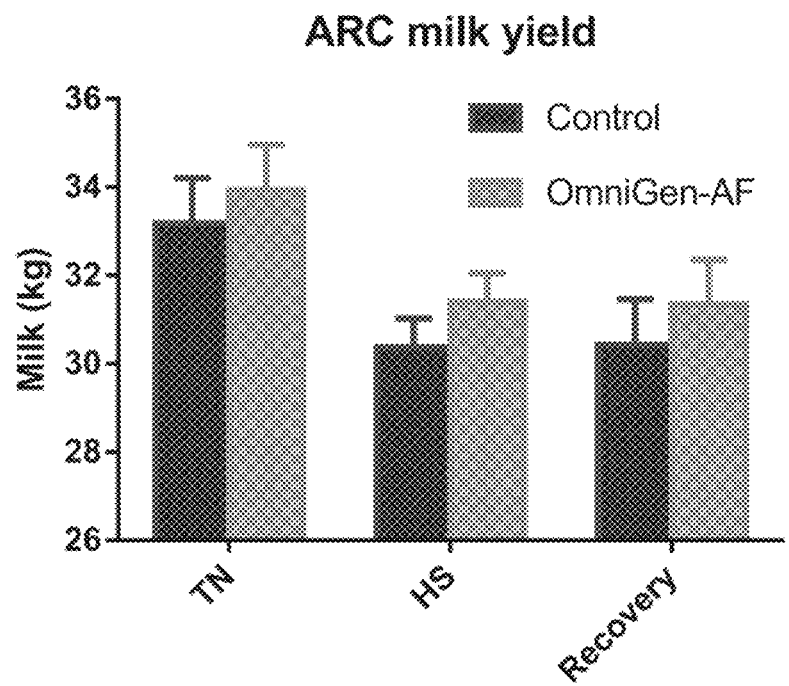
FIG. 2 is a bar chart illustrating milk yield for control cows and cows that have been administered the disclosed composition during thermoneutral conditions (TN), heat stress conditions (HS), and recovery conditions (Recovery).
Figure 3:
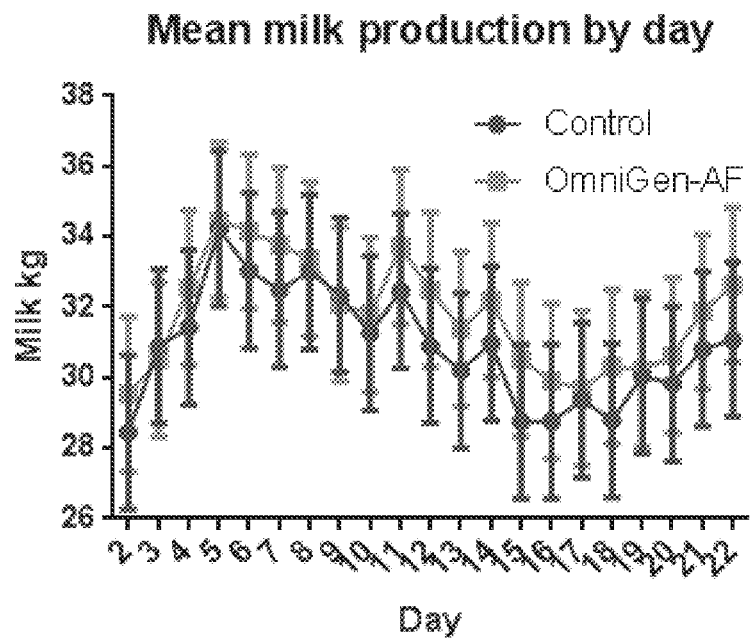
FIG. 3 is a graph illustrating mean milk production by day for control cows and those that have been administered the disclosed composition.
Figure 4:
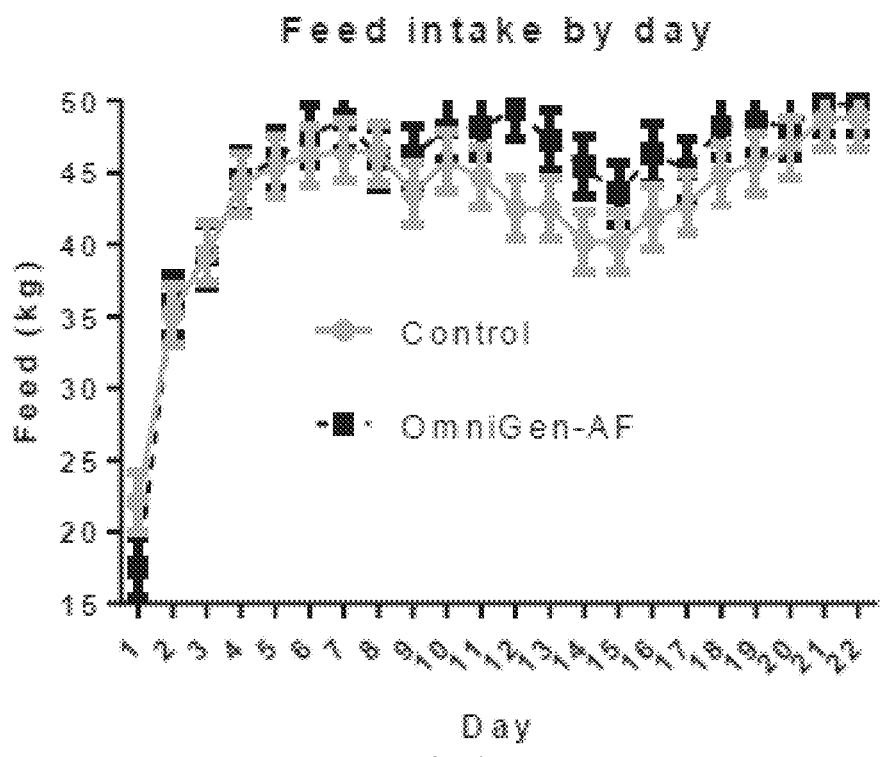
FIG. 4 is a graph illustrating feed intake by day for control cows and those that have been administered the disclosed composition.
Figure 5:
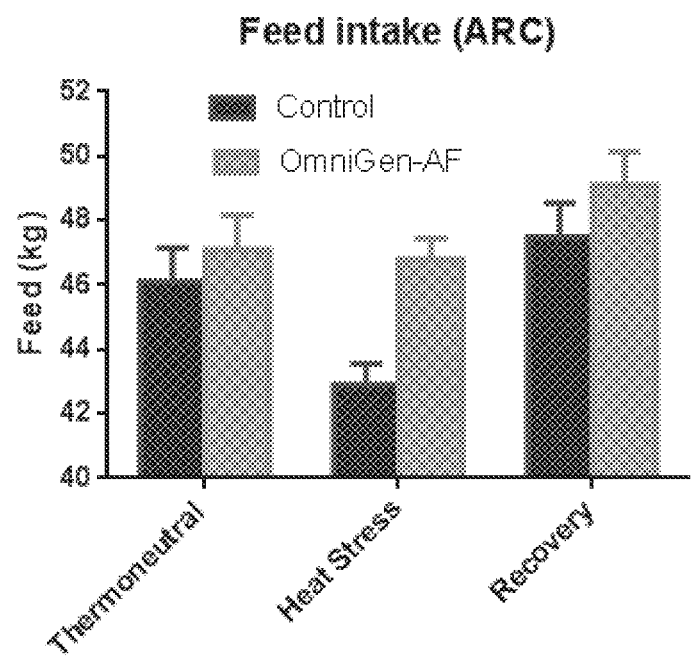
FIG. 5 is a bar chart illustrating feed intake for control cows and cows that have been administered the disclosed composition during thermoneutral conditions, heat stress conditions, and recovery conditions.

There was a period effect on milk yield (P<0.01) during the environmental room (ARC) phase associated with a decline in milk yield in both groups during HS. Milk yield at the ARC (P <0.23) did not differ between control and OG fed groups (FIGS. 2, 3), however, there was a numerical advantage (1.1 kg/day) for cows fed OG during HS (P<0.26) which was similar to the pattern in milk yield noted during the on-farm phase Feeding the disclosed composition to heat stressed dairy cows maintained feed intake during heat stress. Feed intakes in the two groups did not differ during TN but was higher during HS in OG-fed cows (46.8 kg/d and 42.9 kg/d, P<0.01, FIGS. 4, 5; Table 1).

Figure 6:
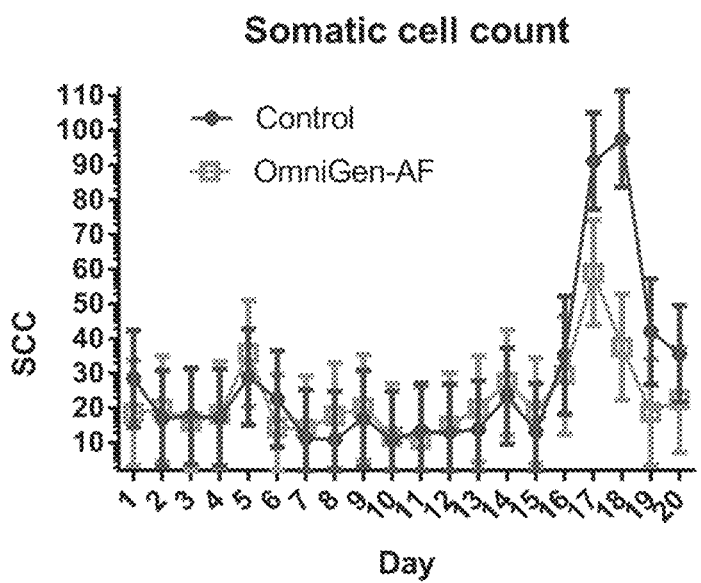
FIG. 6 is a graph illustrating somatic cell count by day for control cows and those that have been administered the disclosed composition.

Milk protein (%) and fat (%) were lower in OG-fed cows (Table 1) during HS but not during TN. There was no difference in FCM or protein yield between treatments. Cows fed OG displayed decreased somatic cell count (SCC) compared to control cows (59.4 and 26.3×1000, P<0.03; Table 1) with the greatest difference during the recovery period (FIG. 6). There was a spike in SCC around day 5 (TN) and during recovery around day 17 (FIG. 6).

TABLE 1

Effects of OmniGen-AF supplementation in heat-stressed lactating dairy cows

| | Control | | | OmniGen-AF | | | | |
|---|---|---|---|---|---|---|---|---|
| Item | TN | HS | Recovery | TN | HS | Recovery | SEM | P-value |
| Feed intake (kg) | 46.1 | 42.9 | 47.5 | 47.1 | 46.8* | 49.1 | 1.04 | 0.01 |
| Milk yield (kg) | 33.1 | 30.3 | 30.4 | 33.9 | 31.4 | 31.3 | 1.02 | 0.23 |
| Fat (%) | 4.03 | 4.22 | 4.16 | 3.94 | 3.82 | 3.83 | 0.22 | 0.04 |
| FCM (kg/d) | 35.0 | 33.7 | 33.7 | 34.7 | 32.8 | 32.6 | 1.45 | 0.39 |
| Protein | 2.95 | 2.98* | 2.86 | 2.95 | 2.86 | 2.79 | 0.07 | 0.15 |
| Protein (kg) | 0.98 | 0.89 | 0.90 | 1.00 | 0.93 | 0.92 | 0.30 | 0.13 |
| Lactose (%) | 4.87 | 4.85 | 4.99 | 4.89 | 4.78 | 4.96 | 0.08 | 0.61 |
| SCC | 20.3 | 23.9 | 59.4* | 19.6 | 22.9 | 26.3 | 9.12 | 0.03 |

*= P-value ≤ 0.05 and indicates the higher value

Respiration rate and rectal temperatures did not differ between treatments during TN; however, during HS, OG reduced respiration rate, (Table 2, P<0.01) in both environments at 1400 h and in HS animals at 1800 h when environmental heat load was greatest. Rectal temperatures were lower in cows fed OG at 1400 and 1800 h compared to controls when environmental heat loads were maximal.

TABLE 2

Effects of OmniGen-AF supplementation and environment on respiration rate and rectal temperature in lactating dairy cows

| | Control | | | OmniGen-AF | | | | |
|---|---|---|---|---|---|---|---|---|
| Item | TN | HS | Recovery | TN | HS | Recovery | SEM | P-value |
| Resp/min | | | | | | | | |
| 600 | 26.9 | 31.9 | 28.3 | 26.6 | 30.4 | 27.9 | 1.40 | 0.40 |
| 1400 | 34.3 | 63.1* | 35.3 | 30.1 | 58.3 | 35.5 | 2.99 | 0.20 |
| 1800 | 34.9* | 60.8* | 32.1 | 29.5 | 52.4 | 29.7 | 2.62 | 0.01 |
| Rectal Temp (° C.) | | | | | | | | |
| 600 | 38.2 | 38.0 | 37.9 | 38.2 | 38.1 | 38.1 | 0.05 | 0.26 |
| 1400 | 38.0 | 38.7* | 38.0 | 38.1 | 38.5 | 38.1 | 0.09 | 0.77 |
| 1800 | 38.2 | 39.1* | 38.2 | 38.2 | 38.8 | 38.3 | 0.08 | 0.25 |

*P ≤ 0.05 and indicates the higher value.

Figure 7:
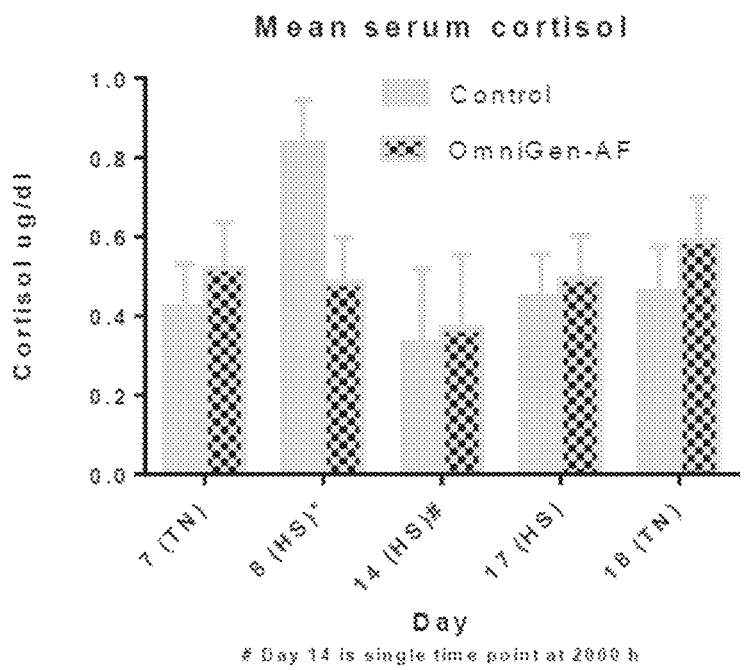
FIG. 7 is a bar chart illustrating mean serum cortisol for control cows and cows that have been administered the disclosed composition during thermoneutral conditions (TN) and heat stress conditions (HS), measured after a certain number of days.

Hormones in plasma are important as potential indicators of the physiological status of a cow and reflect the physiological compensations a cow undergoes at various stages of lactation and exposure to HS. Serum cortisol levels were highest on day 8 (first day of HS, FIG. 7). This is in agreement with prior reports that acute but not chronic HS is associated with increases in circulating cortisol concentrations (Christian and Johnson, 1972, Wise et al., 1988). OG treated cows had significantly lower serum cortisol on day 8 (0.8372 vs. 0.4838 µg/dL for control and OG respectively, P<0.006) and did not differ on other days. This suggests that OmniGen may reduce impact of acute stress on the cortisol response in lactating dairy cows.

Figure 8:
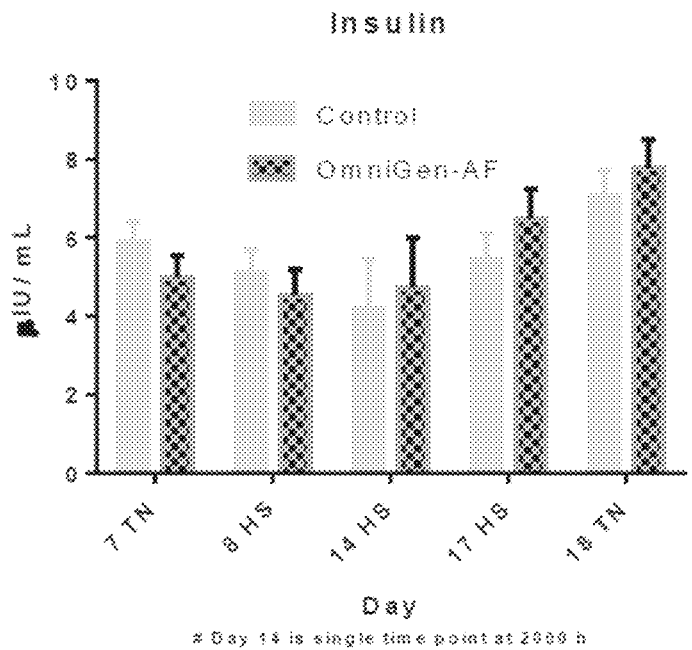
FIG. 8 is a bar chart illustrating mean serum insulin levels for control cows and cows that have been administered the disclosed composition during thermoneutral conditions (TN) and heat stress conditions (HS), measured after a certain number of days.
Figure 9:
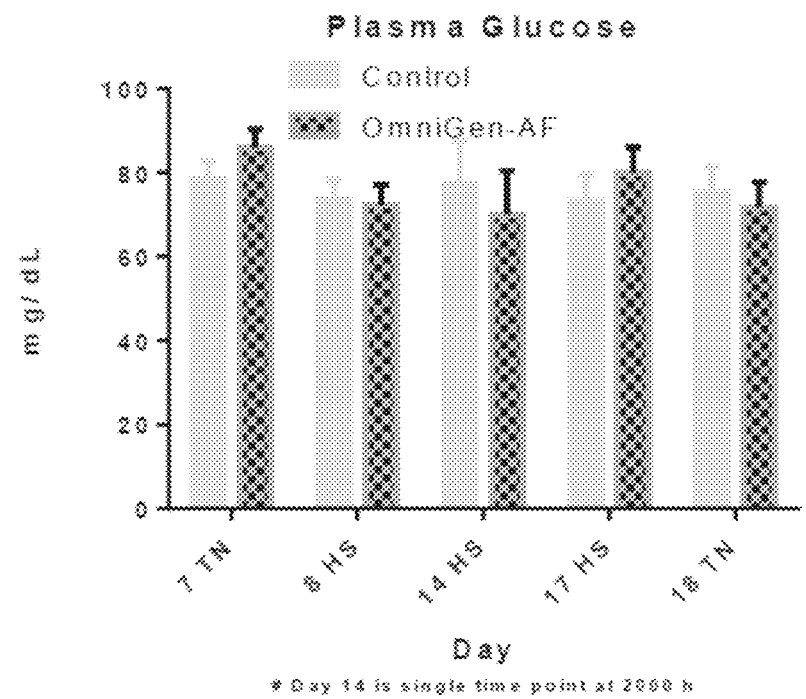
FIG. 9 is a bar chart illustrating mean serum glucose levels for control cows and cows that have been administered the disclosed composition during thermoneutral conditions (TN) and heat stress conditions (HS), measured after a certain number of days.

Serum insulin and plasma glucose levels (FIGS. 8 and 9) were not different between groups (P=0.8248 and 0.945). Serum insulin concentrations in both groups rose during the latter part of the HS period and during the recovery period. The reason for this pattern is unknown.

Figure 10:
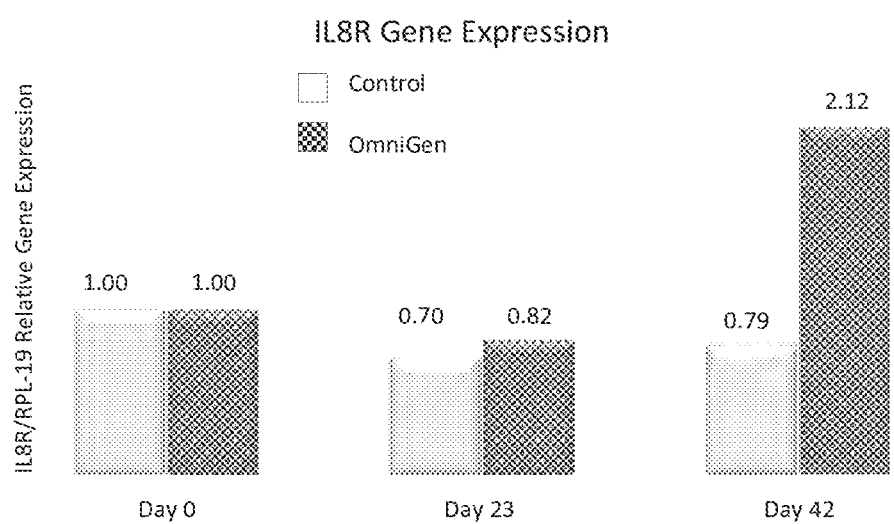
FIG. 10 is a bar chart illustrating IL8R receptor gene expression leukocytes in lactating control cows and cows that have been administered the disclosed composition during thermoneutral conditions and heat stress conditions, measured after a certain number of days.
Figure 11:
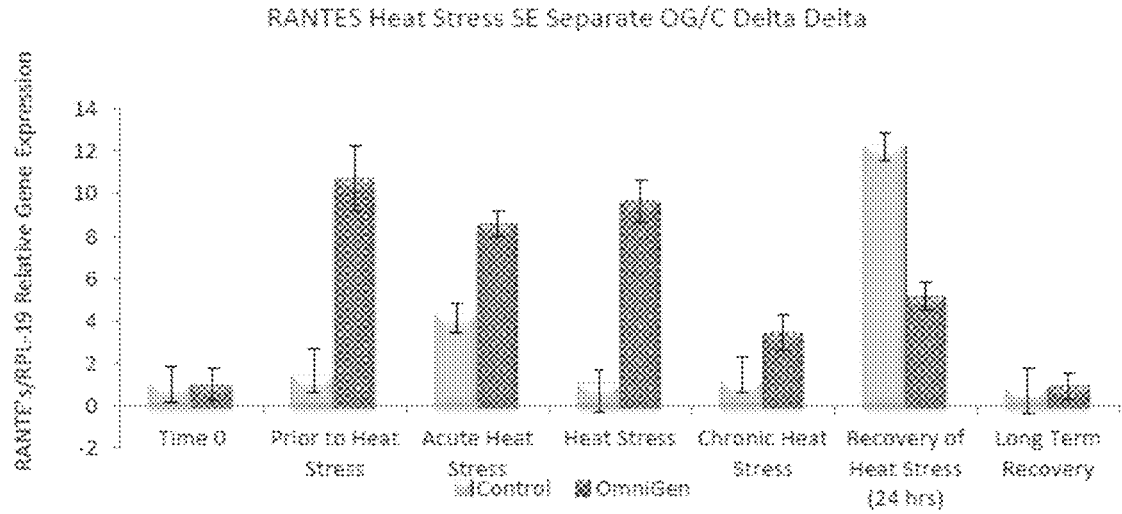
FIG. 11 is a bar chart illustrating RANTES protein levels in control cows and cows that have been administered the disclosed composition prior to heat stress, during acute heat stress, chronic heat stress, heat stress recovery and long-term recovery.

The immune function of cattle on this study was evaluated by looking at the expression of the interleukin-8 receptor (FIG. 10) and expression of Regulated on Activation, Normal T Expressed and Secreted (RANTES) protein (FIG. 11) which is a member of the interleukin-8 family of cytokines.

Heat stress exposure was mild to moderate in this study. The threshold for heat stress in lactating dairy cows is a THI >68, respiration rates >60 bpm, and rectal temperatures >38.5° C. (Zimbleman et al., 2009). OG reduced impact of thermal stress on stress of lactating dairy cows. Cows fed OG had reduced rectal temperatures and respiration rates during periods of peak thermal load. Respiration rates in treated cows did not exceed 60 bpm and mean rectal temperatures were 0.2 to 0.3° C. cooler. OG fed cows displayed higher feed intakes during HS as well. Cows fed OG also displayed a lower cortisol spike on the first day of heat stress.

Milk yield decreased with heat stress in both control animals and the OG fed animals. However, feed intake was unchanged in cows fed OG and milk yields were numerically higher. Changes in SCC were consistent between groups. Cows fed OG displayed decreased SCC compared to control cows with the greatest difference during the recovery period.

Serum cortisol levels were similar to previous findings (Christison and Johnson, 1972) and increased within the first day of heat exposure. The animals in the ARC had higher cortisol levels compared to published levels, but the confinement and changes in surrounding from the dairy to the ARC may account for some of the changes.

Cytokine (RANTES) gene expression was higher in cows fed OG during the HS portion of the study but not during recovery. The elevated cytokine gene expression may be associated with improved immune function in cows fed OmniGen-AF.

Example 3

Figure 12:
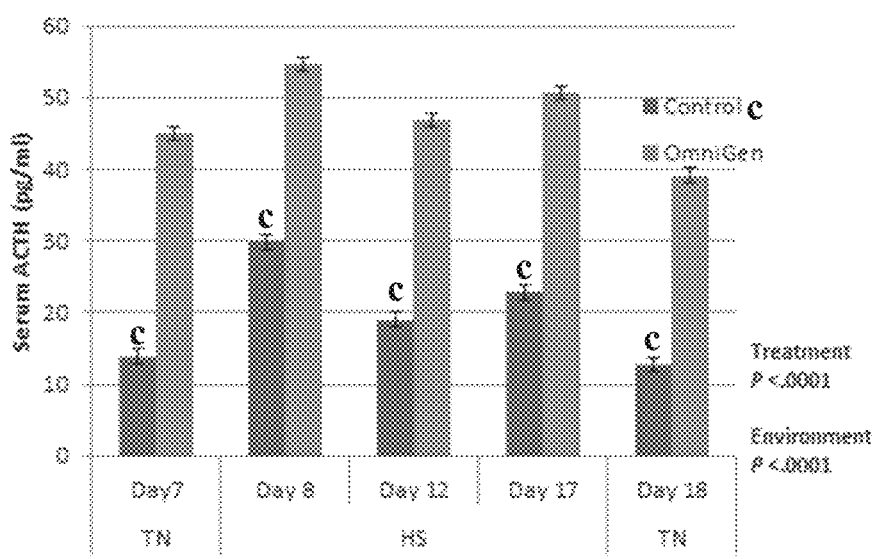
FIG. 12 is a bar chart illustrating serum ACTH levels in control cows and lactating dairy cows that have been administered the disclosed composition during thermoneutral conditions (TN) and heat stress conditions (HS), measured after a certain number of days.

Embodiments of the disclosed composition, such as OmniGen-AF® composition comprising between 15% and 40% silica, between 50% and 81% mineral clay, between 1.0% and 5.0% β-glucans, between 0.05% and 3.0% β-1,3 (4)-endoglucanohydrolase and between 1% and 8.0% mannan (OG), have been demonstrated to reduce physiological measures of heat stress (e.g., body temperature, respiration rate, and water intake) in cattle subjected to temperature and humidity conditions above their thermoneutral zone. Concomitantly, in OG-fed animals, feed intake was significantly increased and milk yield was numerically increased during periods of thermal stress. Furthermore, measures of immune function were improved along with reduced cortisol concentrations during acute heat stress. Paradoxically, adrenocorticotrophic hormone (ACTH) which regulates cortisol secretion from the adrenal cortex was significantly increased in animals fed OG (FIG. 12). This suggests that either the adrenal is less responsive to ACTH or that corticoid binding globulin is increased in animals fed OG. Both conditions would result in increased ACTH secretion from the pituitary since negative feedback in both cases would be reduced. The objective of this study is to determine if feeding OG to lactating dairy cows decreases adrenal responsiveness to ACTH or increases corticosteroid binding globulin in either thermoneutral or heat stress conditions.

Heat stress in dairy cows may result in reductions in dry matter intakes and milk yields and elevated somatic cell counts, respiration rates, body temperature and plasma heat shock protein and serum cortisol. Feeding OG may reduce the impact of heat stress on these measures of stress response. Feeding OG to non-heat stressed lactating dairy cows for 52 days prior to a heat stress bout may increase the expression of immune markers of neutrophil function (L-selectin, IL8-R and IL-1B) associated with altered secretion of cortisol from the adrenal gland. This may be associated with reduced cortisol secretion in response to ACTH infusion in cows fed OG. Heat stress may reduce the expression of immune markers of neutrophils even in cows supplemented with OG. However, the reduced cortisol secretion response may also be present in heat stressed dairy cows fed OG.

Experimental Design:

Animal Selection and Treatment Assignment:

Thirty lactating dairy cows will be assigned to one of two treatments (15 head/treatment). Treatment 1 cows will be fed a control diet without OG, and Treatment 2 cows will be fed the control diet plus OG. OG will be pre-blended in a grain mix to provide 56 g/h/d. Each cow will be housed in an individual tie-stall where individual feed and water intake can be controlled and recorded prior to moving to the Agricultural Research Center (ARC). After 45 days on study, all cows will be given a low dose ACTH challenge (20 mg) via tail vein infusion, and blood samples will be taken at time zero, 1 hour, 4 hours and 8 hours after ACTH challenge. Subsequently, a subgroup of 12 cows, which have been on their respective diets on a commercial dairy for 55 days prior to the moving to the ARC environmental controlled rooms, will be added. From the 30 original cows assigned to treatments, 6 cows from each treatment will be selected for the trial and will continue on their respective treatment diets while in the ARC. Cow will be the experimental unit.

Blood Sample Schedule:

Blood samples will be collected on all treatment cows while at the commercial dairy at days 1, 21 and 42 after initial treatment assignment. On days 45-50 ten cows each day will be subjected to low dose ACTH challenge. On each sampling day, approximately 2 hours after the morning feeding, cows will be restrained in headlocks, taking care to avoid stressing the animals; tail vein blood samples will be obtained from each animal and then infused via tail vein or tail artery with 20 µg (=2IU) of a synthetic analogue of ACTH (ACTH1-24, Synacthen®-Novartis Pharma AG-Stein, CH). Blood samples will also be taken 30 and 60 minutes after ACTH injection, leaving cows restrained in the head locks. All the blood samples will be collected in vacuum Li-heparin tubes, and immediately stored in iced water. In the blood samples, packed cell volume (PCV) will be determined and, after centrifugation (3500 g for 16 min.

at 6° C.), plasma cortisol will be measured by the RIA method (Coat-A-Count; DPC, Los Angeles, Calif., USA). The integrated response of cortisol over 60 min will be evaluated as area under the curve. For the statistical evaluation, data will be subjected to ANOVA using GLM procedure (SAS Inst. Inc., Cary, N.C., release 9.1) including in the model cow, dietary treatment (control or OG) stage of lactation as main factors. A repeated measures analysis will also be conducted on the challenge data.

At arrival to the ARC, cows will be weighed, fitted with halters and blood samples collected. Cows will remain in the ARC chambers for 21 days, the first 7 days at thermal neutral (TN) conditions followed by 10 days of heat stress (HS) and then 4 days in TN conditions. On d 7 of TN, d 8 (HS), d 17 (HS), d 18 (TN) and d 21 (TN) cows will be bled in 4 h intervals at 0400, 0800. 1200, 1600, 2000, and 2400 h following a low dose (20 mg) of ACTH infused via the tail vein.

Physiological/Behavior Metrics:

To assess the effectiveness of the imposed heat stress model, known physiological and behavioral responses will be measured and recorded daily. These will include feed intake, water consumption, milk yield, milk somatic cell concentrations (cells/ml), respiration rate, rectal temperature and skin temperature measurements (3×/d at 0600, 1400 and 1800 h). Milk samples will be collected and stored in vials containing bronopol tablets for preservation and stored at 4° C. until analysis. Analysis will be done by infrared analysis. All treatment and health events will be recorded daily.

Blood collected for immune biomarkers will be collected and preserved according to protocol (Wang, et al., 2003). The immune biomarkers neutrophil L-selectin, IL8-R and IL-1B will be evaluated on each sample. In addition, on days 17 and 18 from the 0800 and 1600 h samples, neutrophils will be purified and assessed for RANTES (regulated on activation, normal T cell expressed and secreted), phagocytosis ability or ROS (reactive oxygen species) generation. Ionized serum calcium will also be determined on samples collected on days 1, 7, 17, 18 and 21. Blood samples collected on day 1 of arrival to the ARC and days 7, 8, 12, 17, 18 and 21 will be assayed for Heat Shock Protein (HSP) and cortisol. These samples will be stored on ice until centrifugation (15,000×g) for 15 minutes at 4° C. Plasma will be removed and stored at −20° C. and the buffy coat fraction will be removed and stored in Trizol at −80° C. On days of blood sampling, additional milk samples will be collected at both the AM and PM milking and neutrophils isolated.

An additional possibility is the sampling of fecal cortisol as a noninvasive measure of cortisol output. Another consideration is to measure corticoid binding globuli (CBG). An increase in CBG would reduce effective concentrations of cortisol and cause increases in ACTH.

Example 4

Procedures:

Calf-fed steers (306 head; BW 263.5±18.6 kg; 36 pens) were utilized in a randomized block design experiment. Steers were received over a two-day span at the feedlot. Upon arrival, steers were allowed access to water and were processed, weighed, and allocated to treatment within 12 h. During processing, steers were identified with an individual ear tag, individually weighed, vaccinated with Bovi-Shield Gold One Shot™ (IBR, BVD), Dectomax injectable® (internal and external parasiticide), and Somubac® (*Haemophilus somnus* disease complex. Shrunk BW was a single weight collected at time of processing following arrival. Steers were blocked based on arrival date resulting in two blocks. Within blocks, steers were assigned randomly to one of three treatments by gate sorting every two steers to a pen; pen was then randomly assigned to treatment. Treatments included: a control group (Control): no supplementation with the disclosed composition (OmniGen-AF® [OG] comprising between 15% and 40% silica, between 50% and 81% mineral clay, between 1.0% and 5.0% β-glucans, between 0.05% and 3.0% β-1,3 (4)-endoglucanohydrolase and between 1% and 8.0% mannan) OG supplemented at 4 g/cwt of BW for 28 d (receiving period); and OG supplemented at 4 g/cwt of BW for 215 d (the entire feeding period). Supplementation of OG for both the 28 d and 215 d treatment groups was formulated and added to the daily delivery of the diet prior to feeding. A ninth steer was randomly added to nine pens of the control group and the treatment group that only received OG for 28 d during processing of the $2^{nd}$ block. These 18 steers (9 hd/treatment group) would allow for the selection of one steer from each of these 18 pens to be utilized for the intravenous lipopolysaccharide (LPS) challenge portion of the trial.

At the conclusion of the 28 d receiving period, steers were limit fed for a period of 4 d at 2% BW to obtain an end of receiving period BW. At the conclusion of the 28 d receiving period, OG was no longer supplemented to the group of steers within the treatment group that only received OG for the 28 d of the receiving period; steers within the other OG treatment group (fed for 215 d) continued to receive OG. OG supplementation for the remaining treatment group was recalculated every 30 d to supply 4 g/cwt of BW on average. All steers were implanted with Revalor® XS at the conclusion of the receiving period. During the last 28 d of the finishing period, all cattle were supplemented Optaflexx® ractopamine composition at a rate of 300 mg/hd/d. At the end of the trial, steers were transported 51.5 km to a commercial abattoir and held over-night. The following morning steers were harvested; at which time hot carcass weights (HCW) were recorded. Following a 48-h chill, fat thickness, LM area, and USDA marbling score were determined. Final BW, ADG, and F:G were calculated using HCW adjusted to a standard (63%) dressing percentage.

To evaluate the immune response, two LPS challenges were conducted; a subcutaneous LPS challenge (steers from the Control group and the OG fed for 215 d group) and an intravenous LPS challenge (steers from the Control group and the OG fed for 28 d group). For the subcutaneous LPS, three pens from the Control and the OG fed 215 d treatment group were randomly selected. From the selected pens, 6 steers/pen were randomly selected and challenged with LPS via subcutaneous injection on d 21. On d 21, steers from selected pens were removed from the pen and moved to the processing barn. As each steer was processed, BW was determined and an indwelling rectal probe was inserted. After determining BW, each steer was challenged with a subcutaneous injection of LPS at a rate of 0.5 μg/kg of BW and then returned to the feedlot pen. For the intravenous LPS challenge, on d 25 of the receiving period, 18 steers (nine steers from Control and OG fed for 28 d treatment groups) were randomly selected from the 9 Control and 9 OG fed for 28 d pens that contained 9 steers/pen. Steers were identified and moved into a tie stall barn. After a 3 d adjustment period, steers were fitted with indwelling jugular vein catheters for serial blood collection and indwelling rectal temperature (RT) recording devices, set to record RT at 1-min intervals continuously throughout the immune challenge study. After insertion of the jugular catheter and RT probe, steers were returned to the individual tie stalls and allowed to rest for the remainder of the d.

On the following day, from 0800 to 1600 h, blood samples were collected at 30-min interval; two h prior to the challenge (0800-1000 h) and six h after the challenge (1000-1600 h). At 1000 (0 h), following the collection of the blood sample, steers were administered an i.v. dose of lipopolysaccharide (LPS, 0.5 µg/kg BW; purified from *E. coli* O111:B4; Sigma-Aldrich, St. Louis, Mo.). A final blood sample was collected 24 h post LPS challenge. At each collection point, 9 mL of blood was collected via monovette tubes containing no additive for serum. After collection, blood samples were allowed to clot for 30 min at room temperature and then centrifuged at 2,000×g for 30 min (39.2° F.). Serum was collected and transferred into 1.5 mL microcentrifuge tubes and stored at −112° F. until analyzed. Serum was analyzed for cortisol and pro-inflammatory cytokines (tumor necrosis factor-α, TNF-α; interferon-γ, IFN-γ; and interleukin-6, IL-6).

Feedlot performance data were analyzed as a randomized block design using MIXED procedures of SAS (SAS Institute, Inc., Cary, N.C.). Steers were blocked by arrival date and pen was the experimental unit; model included the fixed effect of treatment and block was a random effect. Immune response data were analyzed as a completely randomized design with repeated measures using the MIXED procedures of SAS; model included fixed effects of treatment and time, treatment×time was used as the error term to test whole plot effect. For both feedlot and immune data, when results of F-test were significant (P<0.05), group means were compared by use of least significant difference. Pair wise differences among least squares means at various sample times were evaluated with the PDIFF option of SAS. Distribution of USDA Quality Grade data were analyzed as a randomized block design using the Glimmix procedure of SAS.

Results:

For the receiving portion of the trial, there was no difference in initial BW (P=0.82), ending BW (P=0.43), ADG (P=0.32), DMI (P=0.76), and F:G (P=0.35) between the three treatments (Table 2). In terms of morbidity related to respiratory diseases, there was no difference (P=0.21) in the % of steers treated (Table 3). There was also no difference in overall feedlot performance; DMI (P=0.89), ADG (P=0.66) and F:G (P=0.90) were similar across the three treatments (Table 2). There was no difference in final BW (P=0.59), HCW (P=0.60), LM area (P=0.31), marbling score (P=0.96), 12th rib fat thickness (P=0.86), or calculated yield grade (P=0.52) between the three treatment groups. The distribution of USDA Quality Grade was analyzed across all three treatments. There was no difference in the amount of USDA Prime, USDA Choice, or USDA Select Quality Grades for all three treatments (Table 3). While there was no statistical difference in terms of the percentage of carcasses grading USDA Choice or greater, the economic significance is still of major importance. Steers supplemented with OG for 215 d had a rate of USDA Choice that was 81.91%, compared to 76.40 for Control steers. With a $13.58 Choice/Select spread (11 Dec. 14), this difference in Choice between the two treatment groups is the equivalent of ~$850 difference in carcass value.

TABLE 3

Receiving period and overall feedlot performance and carcass merit for steers fed no OG (CON), OG during the receiving period (OG-28), or OG for 215 d (OG-215) Treatment groups[1]

| Item | Con | OG-28 | OG-215 | SEM | P-value |
|---|---|---|---|---|---|
| Receiving Performance | | | | | |
| Initial BW (kg) | 259 | 256 | 262 | 3.2 | 0.82 |
| Ending BW (kg)[2] | 300 | 304 | 306 | 3.6 | 0.43 |
| DMI (kg/d) | 7.5 | 7.7 | 7.6 | 0.4 | 0.76 |
| ADG (kg/d)[3] | 1.44 | 1.54 | 1.58 | 0.15 | 0.32 |
| G:F[4] | 0.9 | 0.9 | 0.09 | — | 0.35 |
| Morbidity (%)[5] | 6.9 | 2.0 | 3.0 | 3 | 0.12 |
| Feedlot Performance | | | | | |
| Initial BW (kg) | 261 | 572 | 572 | 6 | 0.87 |
| Final BW (kg)[6] | 649 | 642 | 643 | 11 | 0.59 |
| DMI (kg/d) | 9.80 | 9.80 | 9.88 | 0.3 | 0.89 |
| ADG (kg)[7] | 1.81 | 1.79 | 1.79 | 0.04 | 0.66 |
| G:F | 0.18 | 0.18 | 0.18 | — | 0.90 |
| Carcass Merit | | | | | |
| HCW (lbs) | 409 | 405 | 405 | 3.2 | 0.96 |
| LM area (in[2]) | 94.78 | 91.36 | 94.06 | 1.61 | 0.31 |
| Calculated YG | 3.09 | 3.28 | 3.09 | 0.14 | 0.52 |
| 12th rib fat (cm) | 1.37 | 1.42 | 1.40 | 0.08 | 0.86 |
| Marbling[8] | 503 | 498 | 508 | 24 | 0.96 |
| Prime (%) | 4.49 | 2.13 | 5.32 | 2.32 | 0.53 |
| Choice (%) | 76.40 | 76.60 | 81.91 | 4.50 | 0.59 |
| Select (%) | 19.10 | 21.28 | 13.83 | 4.22 | 0.41 |

[1]CON: No OG; OG-28: OG during receiving, OG: OG for 215 d.
[2]Limit fed at 2% of BW for 4 d prior to single BW to determine ending BW of receiving period
[3]Calculated from ending BW of receiving period
[4]Analyzed as G:F, the reciprocal of F:G.
[5]Overall percentage of steers treated for bovine respiratory disease
[6]Calculated from carcass weight, adjusted to 63% common dressing percent.
[7]ADG for the entire feeding period (including receiving period)
[8]Marbling Score: 400 = Small, 500 = Modest, etc.

Figure 13:
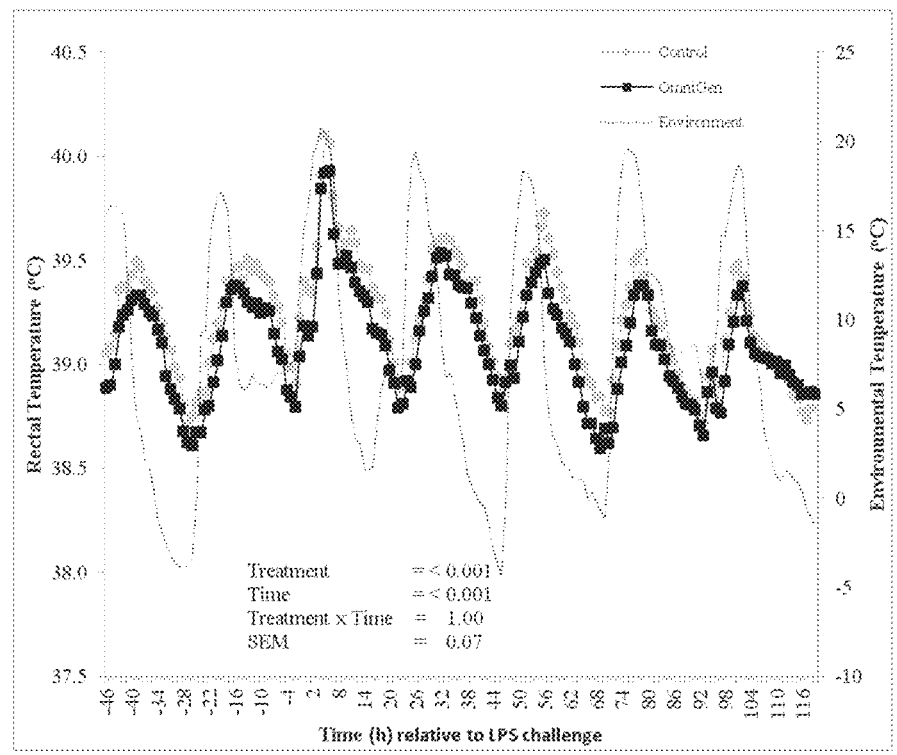
FIG. 13 is a graph showing rectal temperature of newly received steers supplemented with the disclosed composition at a rate of 4 g/cwt (OmniGen) during the receiving period (28 d) or no OmniGen (Control) during a subcutaneous lipopolysaccharide challenge.
Figure 14:
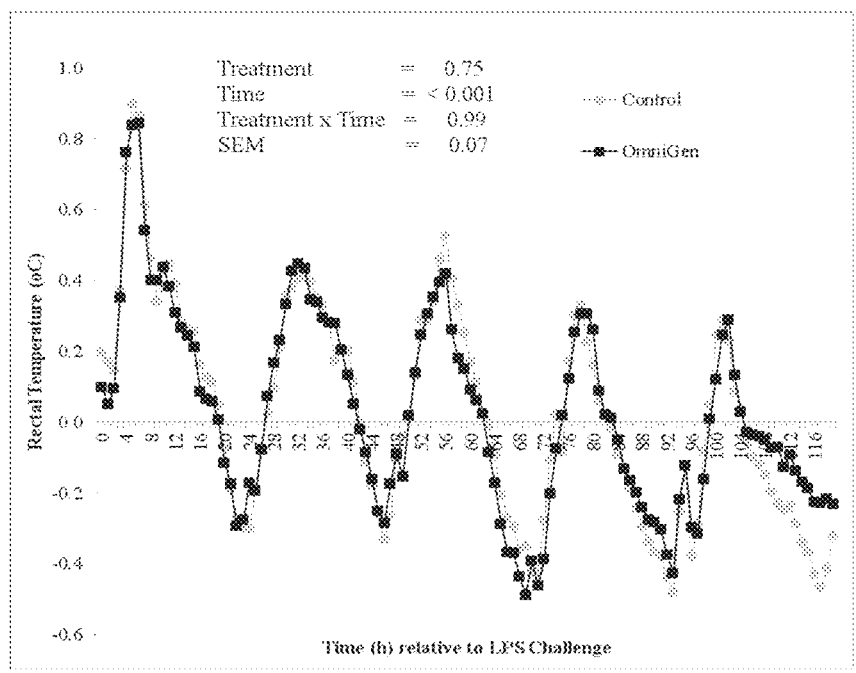
FIG. 14 is a graph showing change in rectal temperature of newly received steers supplemented with the disclosed composition at a rate of 4 g/cwt (OmniGen) during the receiving period (28 d) or no OmniGen (Control) during a subcutaneous lipopolysaccharide challenge.

For the subcutaneous LPS challenge, there was a treatment (P=<0.001) and time (P=<0.001) effect for RT (FIG. 13). Both treatment groups responded to the subcutaneous LPS challenge, with both treatment groups achieving a maximum RT approximately 5 h post challenge (Control=40.10° C. vs. OG=39.92° C.; FIG. 13). Furthermore, both maintained similar patterns (P=1.00) throughout the subcutaneous LPS challenge. Steers in the Control treatment group had an average RT that was greater than the OG treatment group (39.22° C. and 39.07° C., respectively). There was no treatment effect (P=0.75) or treatment×time interaction (P=0.99) for change in RT from baseline (FIG. 14). Again, there was a treatment effect for RT (P=<0.001), but this treatment difference was not observed when comparing the change in RT from baseline between the treatment groups (average change from baseline was 0.03° C. for Control and 0.03° C. for OG).

Figure 15:
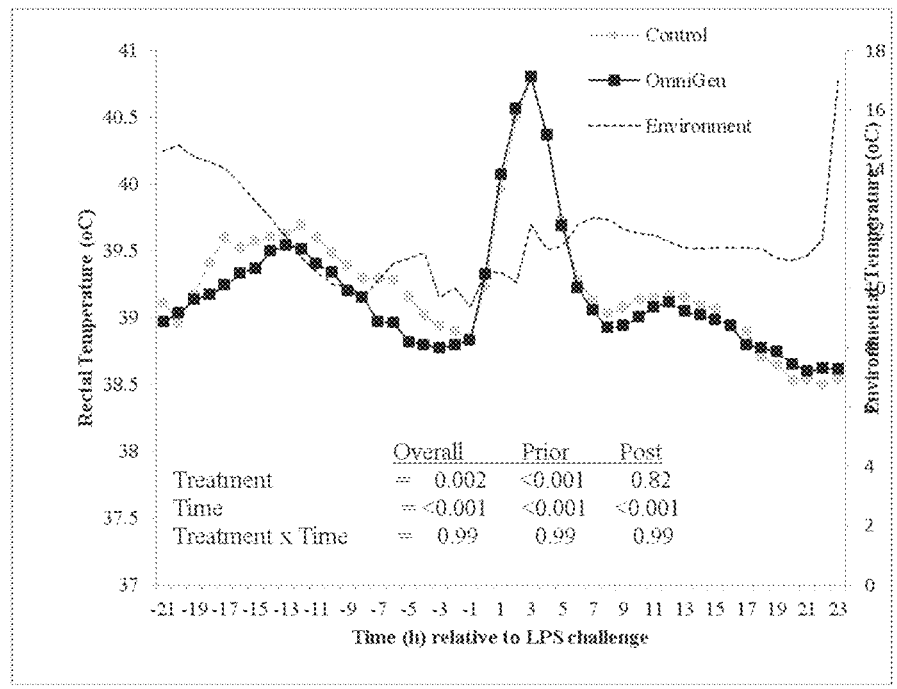
FIG. 15 is a graph showing rectal temperature of newly received steers supplemented with the disclosed composition at a rate of 4 g/cwt (OmniGen) during the receiving period (28 d) or no OmniGen (Control) during a lipopolysaccharide challenge.
Figure 16:
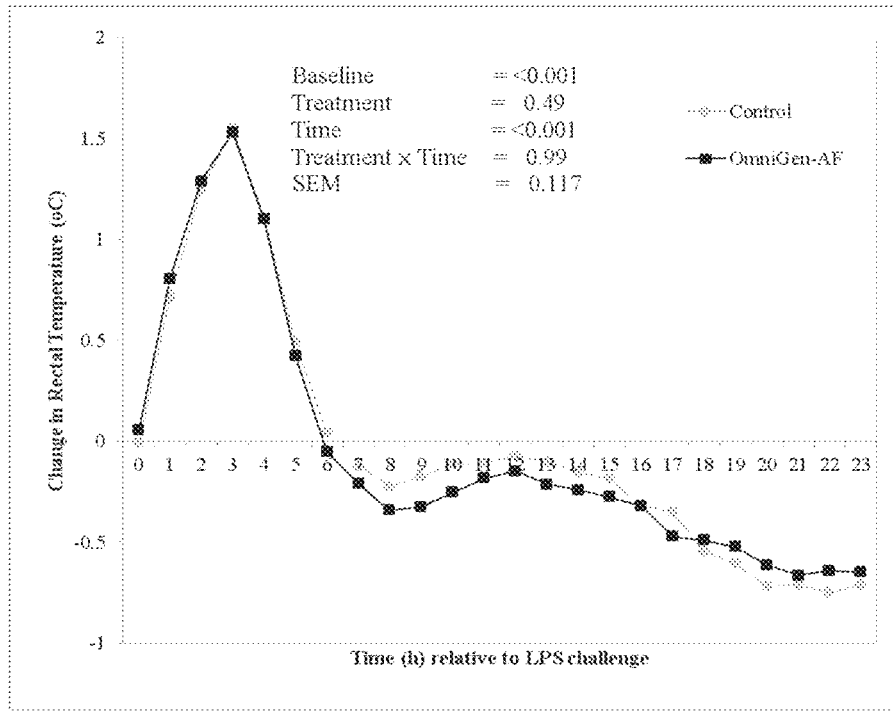
FIG. 16 is a graph showing change in rectal temperature of newly received steers supplemented with the disclosed composition at a rate of 4 g/cwt (OmniGen) during the receiving period (28 d) or no OmniGen (Control) during a lipopolysaccharide challenge.

For the intravenous LPS challenge portion of the trial, there was a treatment (P=0.002) and time effect (P=<0.001), however there was no treatment×time interaction (P=0.99) for RT (FIG. 15). Steers supplemented with OG had a greater RT when compared to Control (39.26° C. vs. 39.17° C., respectively) during the intravenous challenge. This average RT is very similar to the RT that was observed for the steers that were utilized in the subcutaneous LPS challenge. In terms of response to the intravenous LPS challenge, both treatment groups responded to the LPS challenge similarly (P=0.99). For both groups of steers, maximum RT was observed 2.5 h post intravenous LPS administration, and within 6 h, RT had returned to baseline temperatures (−21 to 0 h prior to the challenge: FIG. 15). There was also no treatment effect (P=0.49) or treatment×time interaction (P=0.99) for change in RT from baseline (−21 to 0 h: FIG. 16). Baseline line temperatures were different (P<0.001) between the two treatment groups, but the change from baseline was similar (P=0.49) between the Control and OG supplemented steers (FIG. 16).

Figure 17:
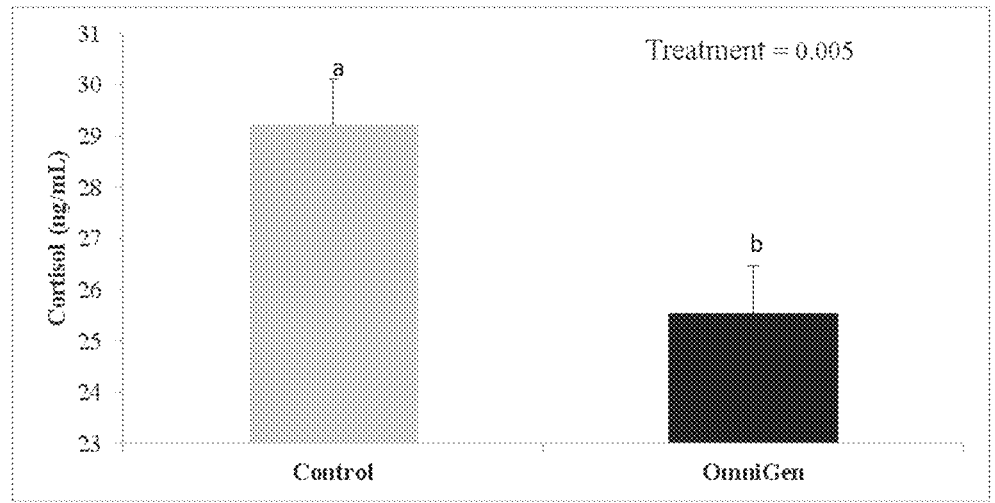
FIG. 17 is a bar graph showing overall cortisol concentrations of newly received steers supplemented with the disclosed composition at a rate of 4 g/cwt during the receiving period (OMN-28) or no OmniGen (CON) during a lipopolysaccharide challenge.
Figure 18:
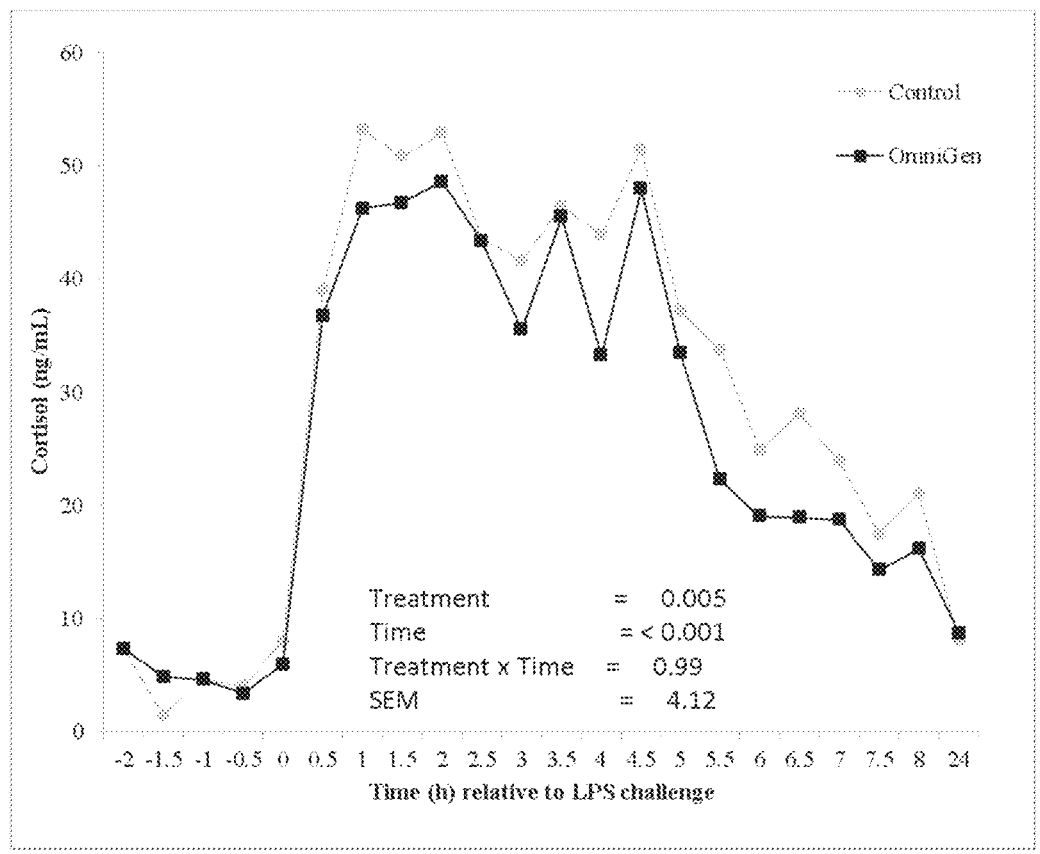
FIG. 18 is a graph showing cortisol concentrations of newly received steers supplemented with the disclosed composition at a rate of 4 g/cwt (OmniGen) during the receiving period (28 d) or no OmniGen (Control) during a lipopolysaccharide challenge.

For serum concentrations of cortisol, there was a treatment (P=0.005) and time effect (P=<0.001); though there was no treatment×time interaction (P=0.99). Steers supplemented OG had decreased concentrations of cortisol, when compared to the CON steers (25.5 vs 29.2 ng/ml, respectively; FIG. 17). In terms of response to the intravenous LPS challenge, both treatment groups responded similarly (P=0.99). Prior to the LPS challenge, both treatment groups had cortisol concentrations below 10 µg/mL. Thirty min after the LPS challenge, cortisol concentrations had increased (P=<0.001) to above 35 µg/mL; cortisol concentrations for both treatment groups did not return to baseline concentrations until 24 h post LPS challenge (FIG. 18).

Figure 19:
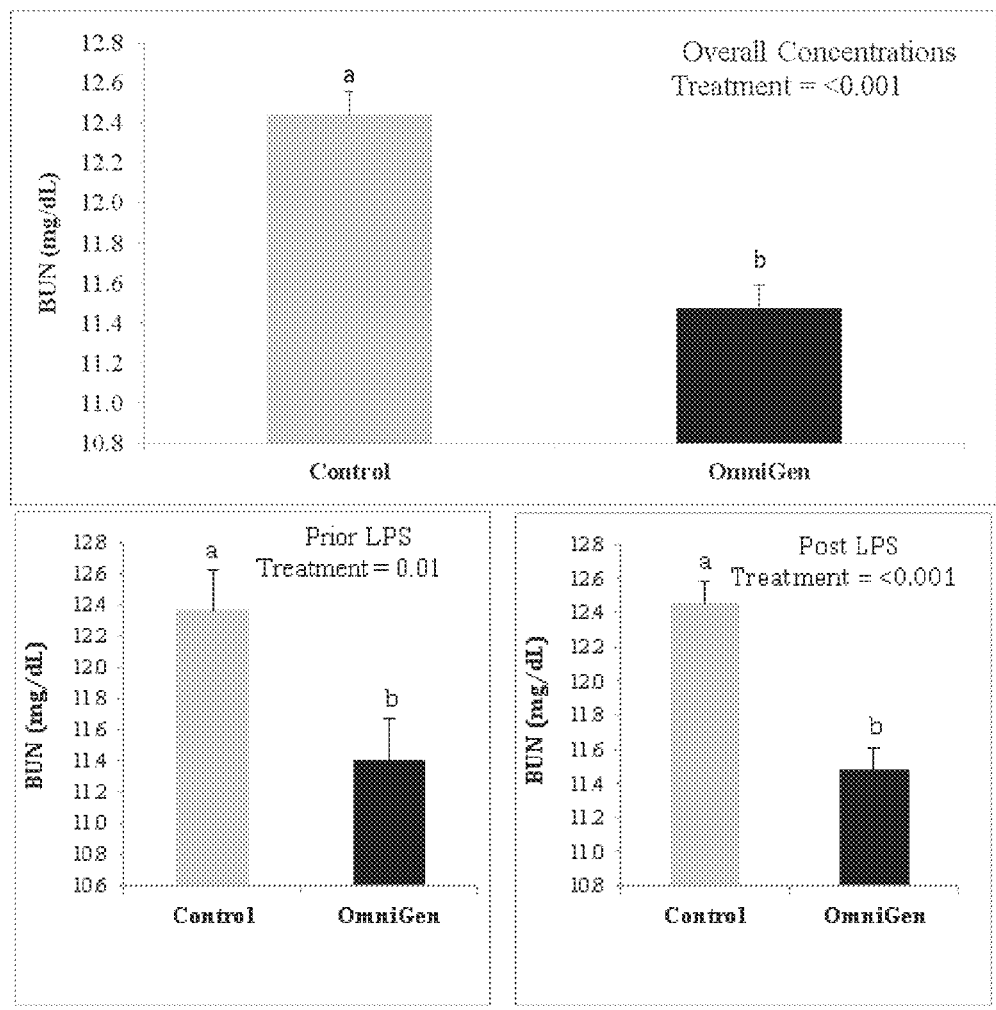
FIG. 19 is a series of bar graphs showing treatment, prior, and post lipopolysaccharide challenge concentrations of blood urea nitrogen (BUN) for newly received steers supplemented with the disclosed composition at a rate of 4 g/cwt (OmniGen) during the receiving period (28 d) or no OmniGen (Control).
Figure 20:
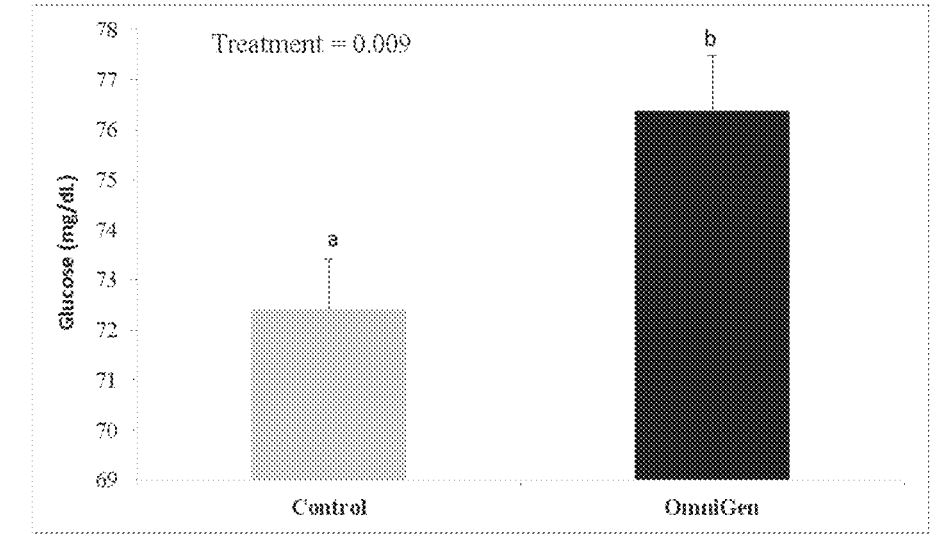
FIG. 20 is a bar graph showing treatment concentrations of glucose concentrations for newly received steers supplemented with the disclosed composition at a rate of 4 g/cwt (OmniGen) during the receiving period (28 d) or no OmniGen (Control) during a lipopolysaccharide challenge.
Figure 21:
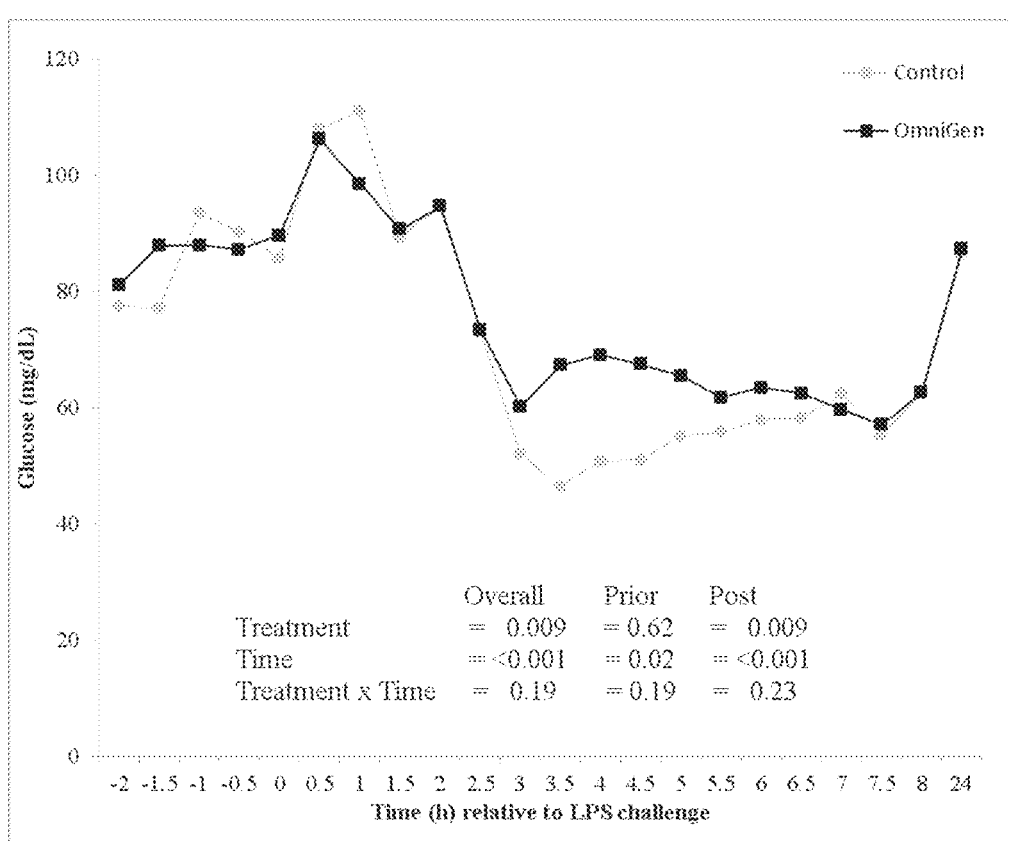
FIG. 21 is a graph showing glucose concentrations of newly received steers supplemented with the disclosed composition at a rate of 4 g/cwt (OmniGen) during the receiving period (28 d) or no OmniGen (Control) during a lipopolysaccharide challenge.
Figure 22:
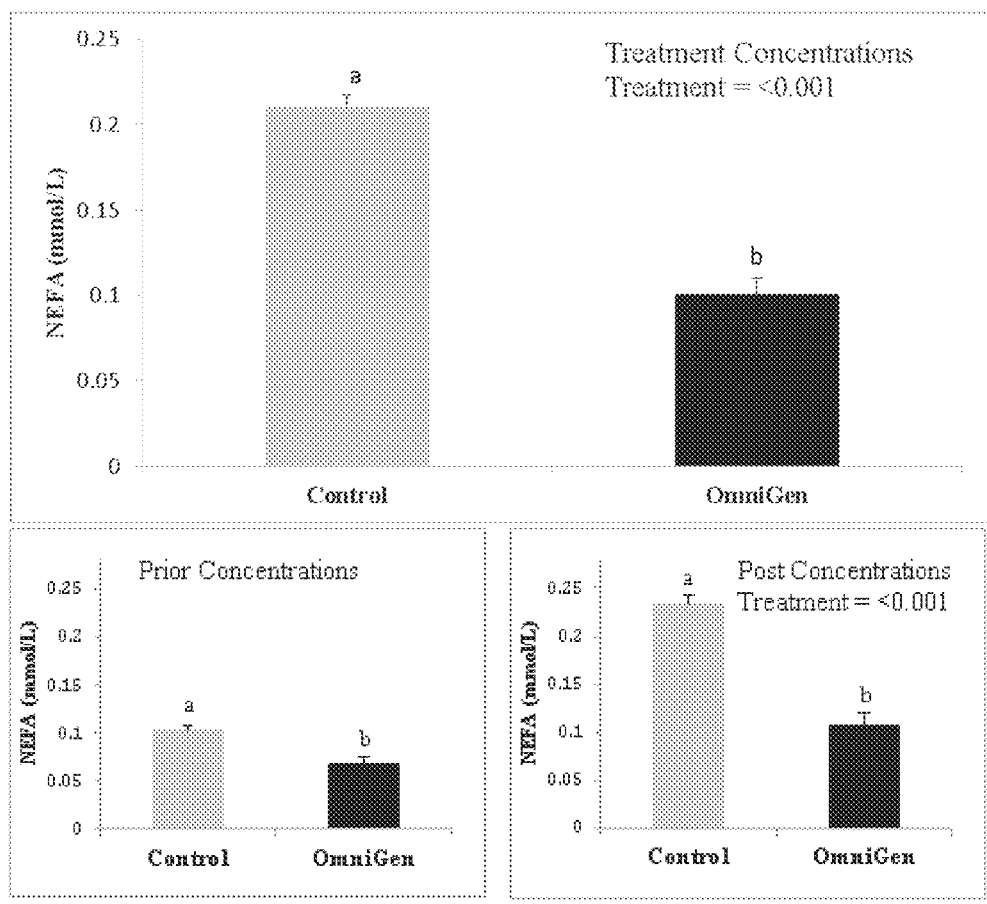
FIG. 22 is a series of bar graphs showing treatment, prior, and post lipopolysaccharide challenge concentrations of non-esterified fatty acids of newly received steers supplemented with the disclosed composition at a rate of 4 g/cwt (OmniGen) during the receiving period (28 d) or no OmniGen (Control).

Blood urea nitrogen (BUN), non-esterified fatty acids, and glucose were analyzed to evaluate metabolic alterations during the intravenous LPS challenge. For BUN's, there was a treatment (P=<0.001) and time (P=<0.001) effect, but there was no treatment×time interaction (P=0.99). Control steers had a greater (P=<0.001) concentration of BUNs when compared to the OG supplemented steers (FIG. 19). This difference in BUNs was observed prior (P=0.01) and post LPS challenge (P=<0001). Regardless of the LPS challenge, Control steers' BUN concentrations were on average 12.4 mg/mL while OG-supplemented steers' BUN concentrations were on average 11.5 mg/mL (FIG. 19.) There was a treatment (P=0.009) and time (P=<0.001) effect for glucose concentrations; no treatment×time interaction (P=0.19). Serum glucose concentrations were greater (P=<0.001) for OG-supplemented steers, when compared to Control steers (76.4 mg/mL vs. 72.4 mg/mL, respectively; FIG. 20). This difference in glucose was not apparent prior to the LPS challenge, as baseline concentrations (−2 to 0 h) were similar (0.62; FIG. 21). However, following the LPS challenge, while both treatment groups had a decrease in serum glucose, this reduction in glucose was greater (P=0.009) in the Control steers, when compared to the OG-supplemented steers (FIG. 21). Prior to the LPS challenge, both treatment groups maintained serum glucose concentrations greater than 75 mg/mL. However, following the LPS challenge (1 h post LPS challenge) serum glucose concentrations started to decrease, and continued to decrease until 3.5 h after administrations of the LPS challenge (FIG. 21). During this decrease in glucose concentrations, concentrations in the Control steers decreased to a greater extent than the OG-supplemented steers. While this decrease of glucose concentrations did not result in a treatment×time interaction, this decrease did result in an overall treatment difference between the two treatment groups (FIG. 21). There was a treatment (P=<0.001) and time (P=<0.001) effect, and a tendency for a treatment×time interaction (P=0.007) for serum NEFA concentrations. Steers within the Control treatment group had greater (P=<0.001) serum NEFA concentrations, when compared to OG-supplemented steers (FIG. 22). This difference in NEFA concentrations was present prior (P=0.006) to the intravenous LPS challenge. However, following the LPS challenge these differences were even greater (P=<0.001: FIG. 22). Prior to the LPS challenge, NEFA concentrations for Control steers were 0.10 mmol/ml while OG-supplemented steers were 0.07. However, following the LPS challenge, NEFA concentrations in the Control steers increased to 0.23 mmol/mL while the OG-supplemented steers only increased to 0.11 mmol/mL.

Figure 23:
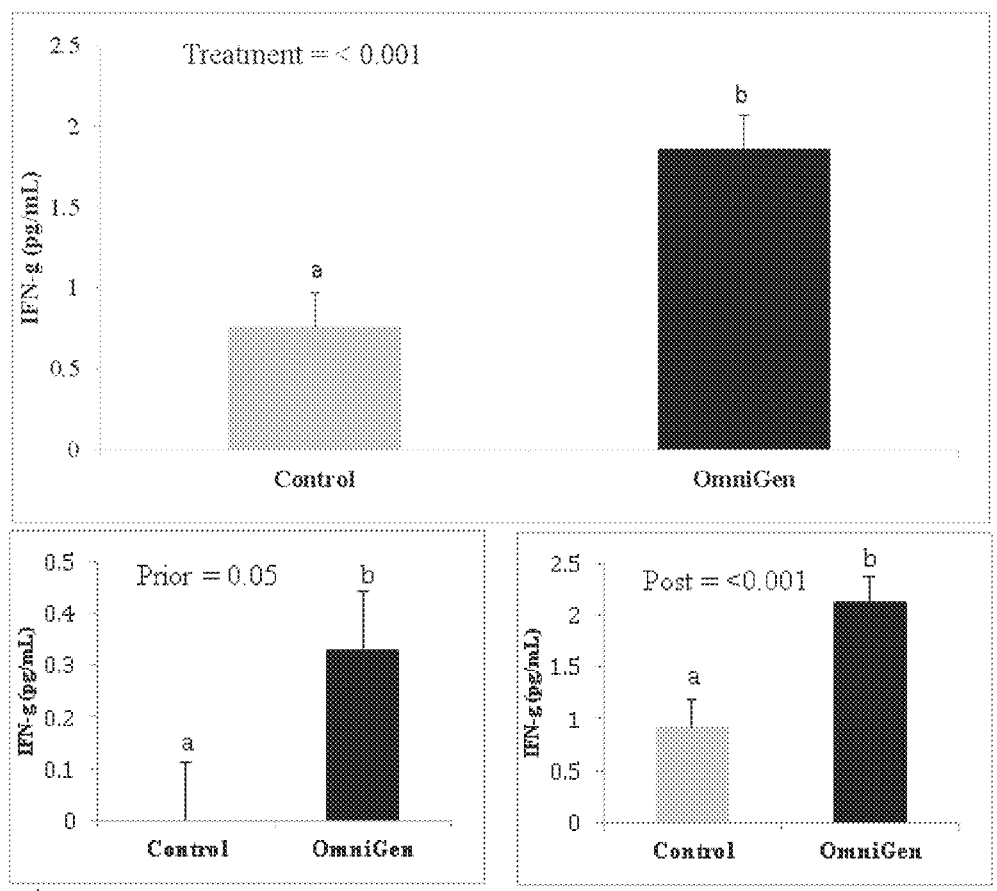
FIG. 23 is a series of bar graphs showing treatment, prior, and post lipopolysaccharide challenge concentrations of interferon-γ concentrations of newly received steers supplemented with the disclosed composition at a rate of 4 g/cwt (OmniGen) during the receiving period (28 d) or no OmniGen (Control).
Figure 24:
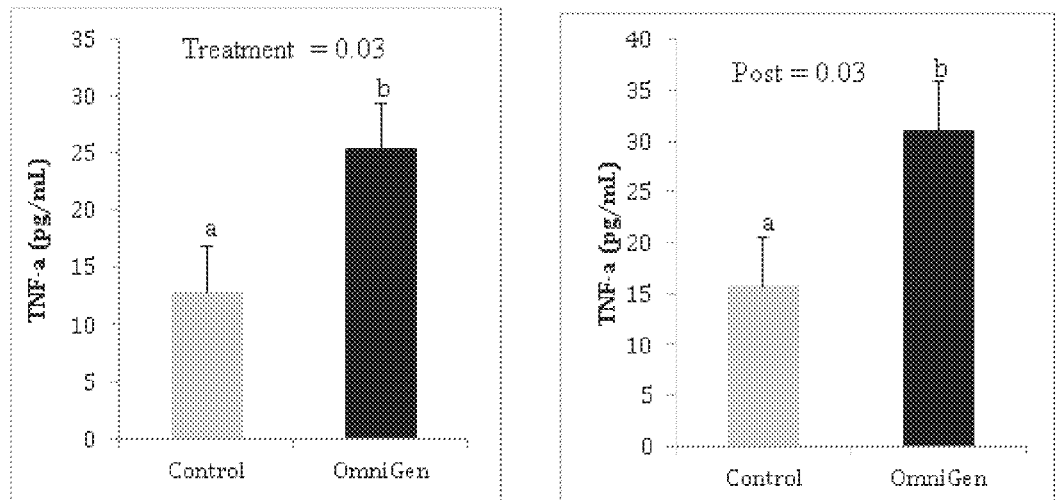
FIG. 24 is two bar graphs showing treatment and post lipopolysaccharide challenge concentrations of tumor necrosis-α (TNF-α) overall and post LPS challenge concentrations of newly received steers supplemented with the disclosed composition at a rate of 4 g/cwt (OmniGen) during the receiving period (28 d) or no OmniGen (Control).
Figure 25:
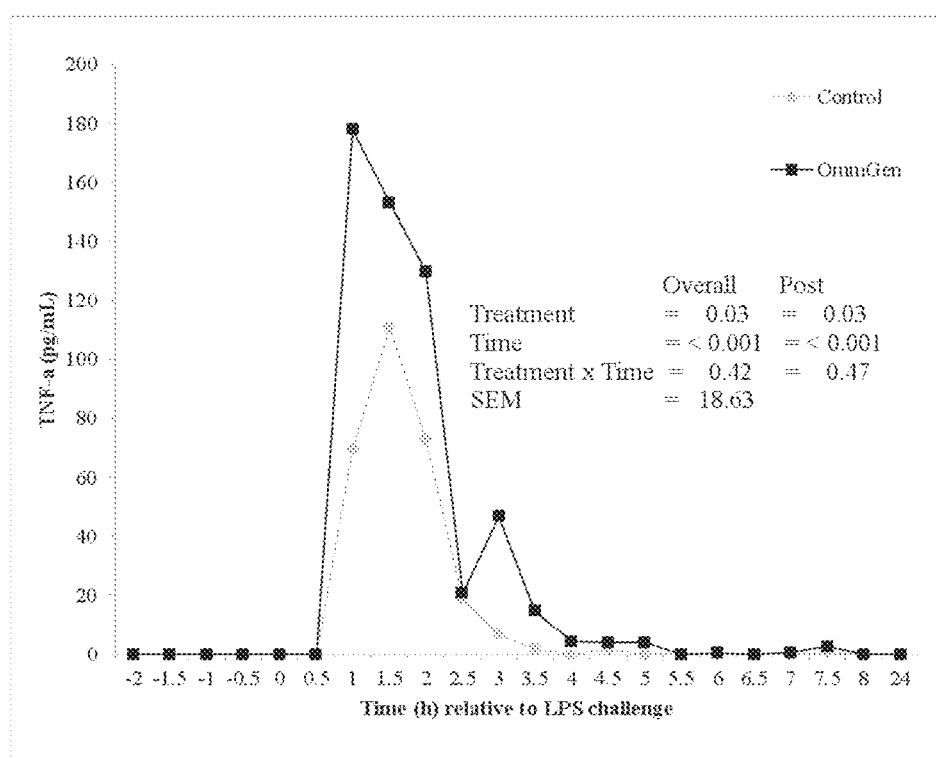
FIG. 25 is a graph showing tumor necrosis-α (TNF-α) concentrations of newly received steers supplemented with the disclosed composition at a rate of 4 g/cwt during the receiving period (28 d) or no OmniGen (Control) during a lipopolysaccharide challenge.
Figure 26:
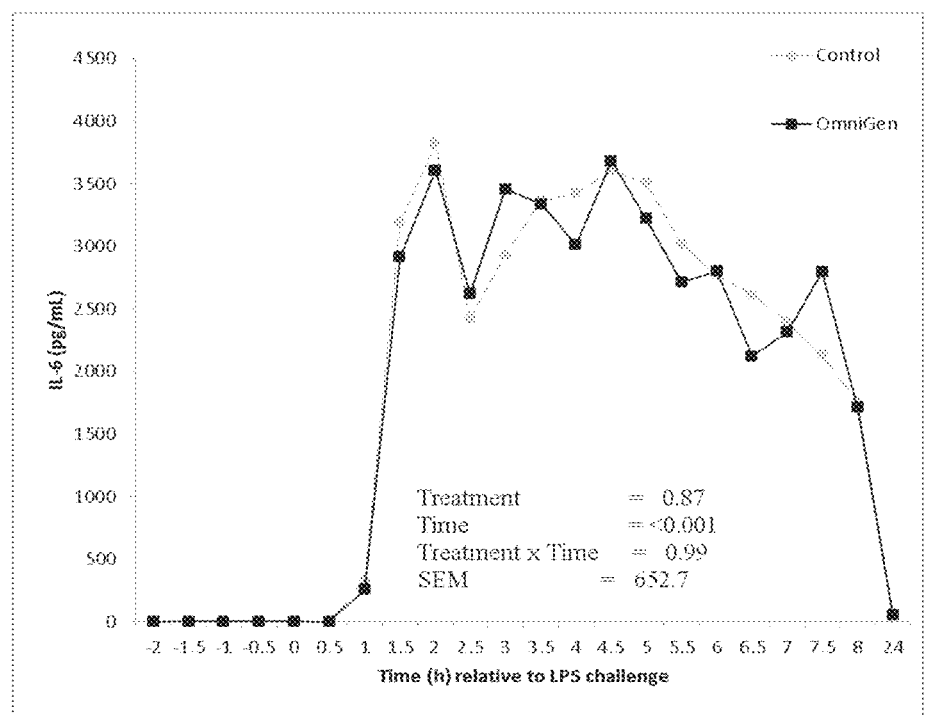
FIG. 26 is a graph showing interleukin-6 (IL-6) concentrations of newly received steers supplemented with the disclosed composition at a rate of 4 g/cwt (OmniGen) during the receiving period (28 d) or no OmniGen (Control) during a lipopolysaccharide challenge.

There was a treatment (P=<0.001) and a time effect (P=<0.001) for the pro-inflammatory cytokine IFN-γ; there was no treatment×time interaction (P=0.77). OG-supplemented steers had a greater production of IFN-γ, when compared to the Control steers (FIG. 23). Prior (P=0.05) and post (P=<0.001) LPS challenge, the concentrations of IFN-γ were greater in the OG-supplemented steers, when compared to the Control steers (FIG. 23). There was also a treatment (P=0.03) and time (P=<0.001) effect for TNF-α; there was no treatment×time interaction (P=0.42). Overall serum concentrations for TNF-α were greater (P=0.03) in the OG-supplemented steers, when compared to the Control steers (FIG. 24). For both treatment groups, prior to the LPS challenge, no detectable concentrations of TNF-α were present, and this no detectable concentrations continued until 0.5 h post challenge (FIG. 25). At 0.5 h, concentrations of TNF-α dramatically increased (P=<0.001) for both treatment groups. Concentrations of TNF-α returned to near baseline (−2 to 0 h) around 4 h after the LPS challenge (FIG. 25). There was only a time effect (P=<0.001) for the pro-inflammatory cytokine IL-6 (FIG. 26). As with TNF-α, prior to the LPS challenge, concentrations of IL-6 were not detectable. However, 1 h after the LPS challenge, concentrations of IL-6 dramatically increased (P=<0.001); reaching maximum concentrations at 2 h post LPS challenge. From 1 to 8 h post LPS challenge, IL-6 concentrations remained elevated above baseline concentrations, and did not return to baseline concentrations until 24 h post LPS challenge (FIG. 26).

Figure 27:
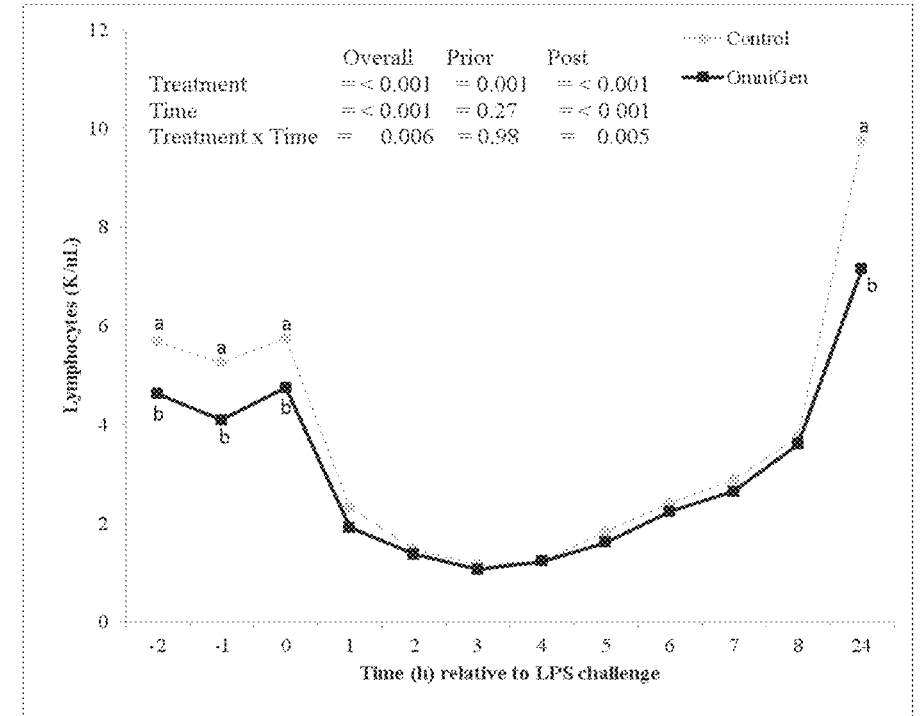
FIG. 27 is a graph showing lymphocyte concentrations of newly received steers supplemented with the disclosed composition at a rate of 4 g/cwt (OmniGen) during the receiving period (28 d) or no OmniGen (Control) during a lipopolysaccharide challenge.
Figure 28:
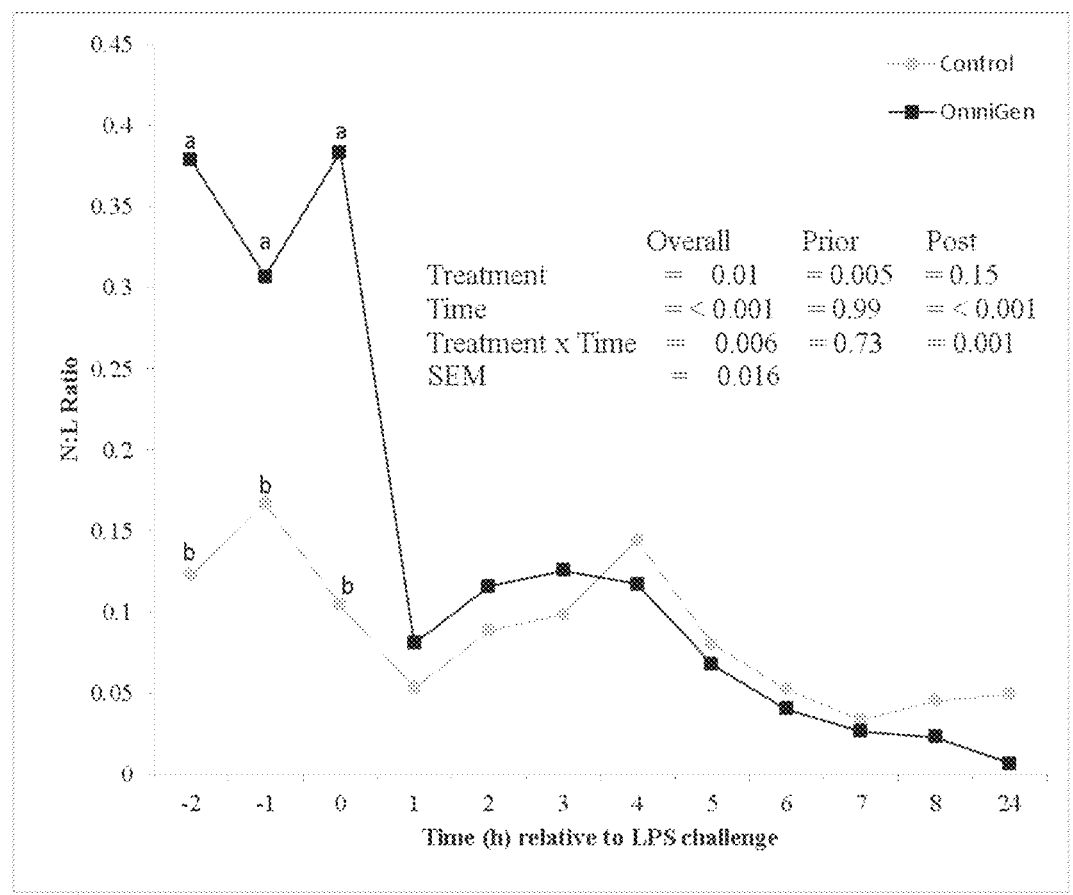
FIG. 28 is a graph showing the neutrophil to lymphocyte ratio of newly received steers supplemented with the disclosed composition at a rate of 4 g/cwt (OmniGen) during the receiving period (28 d) or no OmniGen (Control) during a lipopolysaccharide challenge.

The mean complete blood cell count (CBC) analysis is reported in Table 4. Supplementation of OG did not impact red blood cell counts (P=0.45) or the monocyte percentage (P=0.26). Hemoglobin concentrations (P=0.008), Hematocrit % (P=0.03), and white blood cell concentration (P=0.001) were greater (P=0.008) in Control steers, when compared to OG-supplemented steers. Neutrophil % (P=0.04) and eosinophils concentration (P=0.02) were greater in OG-supplemented steers, when compared to Control steers. For the % of lymphocytes, there was a treatment×time interaction (P=0.006). Prior to the LPS challenge (−2 to 0 h), Control steers had a greater (P=<0.001) concentration of lymphocytes compared to the OG-supplemented steers (FIG. 27). One h after the challenge, there was no difference (P=0.35) between the treatment groups, and from 1 h to 8 h, there was no difference (P=0.66). However, 24 h after the LPS challenge, Control steers had a greater (P=0.005) concentration of lymphocytes (FIG. 27). There was also a treatment×time interaction (P=0.006) for the neutrophil: lymphocyte ratio. Prior to the LPS challenge, the neutrophil: lymphocyte ration was greater (P=<0.001) for OmniGen steers, when compared to Control steers (FIG. 28).

TABLE 4

Mean Complete Blood Cell Count values newly received steers supplemented OG at a rate of 4 mg/cwt during the receiving period (OMN-28) or no OmniGen-AF (CON) during a lipopolysaccharide challenge

| Variables | OmniGen | Control | SEM | P - value TRT | TIME | TxT |
|---|---|---|---|---|---|---|
| Red Blood Cells (mil/μL) | 8.46 | 8.47 | 0.30 | 0.45 | 0.41 | 0.99 |
| Hemoglobin (g/dL) | 10.61 | 10.97 | 0.09 | 0.008 | 0.18 | 0.99 |
| Hematocrit (%) | 31.06 | 32.29 | 0.38 | 0.03 | 0.46 | 0.99 |
| White Blood Cells (K/μL) | 4.47 | 5.42 | 0.12 | 0.001 | <0.001 | 0.88 |
| Neutrophils (%) | 0.43 | 0.26 | 0.05 | 0.04 | <0.001 | 0.34 |
| Lymphocytes (%) | 3.02 | 3.63 | 0.09 | <0.001 | <0.001 | 0.006 |
| Monocytes (%) | 1.06 | 1.14 | 0.20 | 0.26 | <0.001 | 0.23 |
| Eosinophils (K/μL) | 0.07 | 0.04 | 0.005 | 0.02 | 0.76 | 0.76 |
| Neutrophils:Lymphocytes | 0.14 | 0.09 | 0.016 | 0.01 | <0.001 | 0.006 |

Conclusions:

In this study, newly received calf-fed steers supplemented with OG for a period of 28 d (receiving period) or for 215 d (entire feeding period) did not impact feedlot performance or carcass merit. While there was no statistical difference in terms of the percentage of carcasses grading USDA Choice or greater, the economic significance should outweigh the lack of a statistical difference. With a $13.58 Choice/Select spread (11 Dec. 2014), this difference in Choice between the two treatment groups is the equivalent of −$850 in carcass value. Furthermore, supplementation of OG alters the immune response. When challenged with a lipopolysaccharide, OG supplementation appears to prime the pro-inflammatory response (as evident by increased concentrations of IFN-γ and TNF-α). In addition, there was the difference in metabolism that was observed. The increased concentrations of BUN's and NEFA's within the Control steers indicate a possible greater energy need to initiate and sustain an immune response, when compared to the OG-supplemented steers. This increase in greater energy demand is further indicated as the OG-supplemented steers had greater concentrations of serum glucose, when compared to the Control steers. Overall, these results suggest that supplementation of OG may enhance the immune response of calf-fed steers upon feedlot entry.

Example 5

A study was conducted to identify genes expressed by circulating immune cells that are regulated by a commercial embodiment of Composition I. Rats (n=6 per group) were randomly assigned to Composition I and control groups. Composition I was supplemented in the diet at 0.5% in the Composition I group. Total RNA was purified from whole blood and gene expression was analyzed with the use of the Rat Innate and Adaptive Immune Responses RT2 Profiler Polymerase Chain Reaction (PCR) Array (SABiosciences, Qiagen). A total of 84 target genes were present on the array. Gene expression of circulating immune cells was analyzed at seven, fourteen, twenty-one and twenty-eight days of Composition I supplementation. The expression of 67 genes changed following Composition I supplementation across the time points. Table 5 lists the genes with altered gene expression following Composition I supplementation and includes information indicating stimulation (+) or repression (−) of gene expression.

TABLE 5

| Gene | Repressed | Gene | Induced | Reference Genes |
|---|---|---|---|---|
| Crp | − | Ifnb1 | + | Actb |
| Mbl2 | − | Cd80 | + | Ldha |
| Apcs | − | Tlr1 | + | Rplp1 |
| Il5 | − | Tlr6 | + | |
| Ifna1 | − | Mapk8 | + | |
| Ccl12 | − | Nod2 | + | |
| Csf2 | − | Ccr8 | + | |
| Il13 | − | Irak1 | + | |
| Il10 | − | Cd1d1 | + | |
| Gata3 | − | Stat4 | + | |
| Stat3 | − | Il1r1 | + | |
| C3 | − | Faslg | + | |
| Tlr3 | − | Irf3 | + | |
| Ccl5 | − | Ifnar1 | + | |
| Mx2 | − | Slc11a1 | + | |
| Nfkb1 | − | Tlr4 | + | |
| Nfkbia | − | Cd86 | + | |
| Tlr9 | − | Casp1 | + | |
| Cxcl10 | − | Ccr5 | + | |
| Cd4 | − | Icam1 | + | |
| Il6 | − | Camp | + | |
| Ccl3 | − | Tlr7 | + | |
| Ccr6 | − | Irf7 | + | |
| Cd40 | − | Rorc | + | |
| Ddx58 | − | Cd40lg | + | |
| Il18 | − | Tbx21 | + | |
| Jun | − | Casp8 | + | |
| Tnf | − | Il23a | + | |
| Traf6 | − | Cd14 | + | |
| Stat1 | − | Cd8a | + | |
| | | Cxcr3 | + | |
| | | Foxp3 | + | |
| | | Lbp | + | |
| | | Mapk1 | + | |
| | | Myd88 | + | |
| | | Stat6 | + | |
| | | Agrin | + | |
| | | IL33 | + | |

Example 6

Feeding OmniGen-AF® (Composition I or OG; Prince Agri Products, Inc., Quincy, Ill.) at 0.5% of the diet supports immune function in ruminant livestock. Targeted profiling of immune-associated genes in whole blood is an established methodology to evaluate the efficacy of feed additives with immune-altering properties. Higher daily inclusion rate of OG than 0.5% may be required to optimize immune function. The objective of this study was to evaluate the effect of dietary OG inclusion rate (1% vs. 0.5%) on the expression profile of immune-associated genes. Male CD rats (5/treatment) weighing 180-200 grams had ad libitum access to a diet with 0 (control), 0.5 (1×), or 1% (2×) of OmniGen-AF® for 28 days. At the end of the feeding period, whole blood was collected. RNA was purified from whole blood samples and used to generate cDNA that acted as template in the Rat Innate and Adaptive Immune Responses RT$^2$ Profiler PCR array (SABiosciences). Using PROC GLM, cDNA abundance of immune-associated genes was compared between control and supplemented groups (0.5 or 1%) with a P<0.05 cut-off value for significance. Of the 79 immune-associated genes that were expressed above the detection limit in all samples, 16 (7 up-regulated) and 13 genes (8 up-regulated) were altered by 0.5% and 1% OG supplementation, most of which (11 with 6 up-regulated) were altered at both OG inclusion rates. Genes that were up-regulated at both rates include IL13 (0.5%: +3.16, 1%: +3.70 fold-change), IL5 (0.5%: +2.64, 1%: +2.62), Irak1 (0.5%: +2.50, 1%: +1.98), Nod2 (0.5%: +1.83, 1%: +2.02), IFNa1 (0.5%: +1.81, 1%: +2.10), and Cd80 (0.5%: +1.77, 1%: +2.47). Genes that were down-regulated at both inclusion rates include TLR3 (0.5%: −2.22, 1%: −2.39), CxCL10 (0.5%: −2.19, 1%: −2.26), STAT1 (0.5%: −2.07, 1%: −1.99), STAT3 (0.5%: −2.05, 1%: −1.92), and NFκb1 (0.5%: −1.84, 1%: −1.75). The results suggest that OG supplementation inclusion rate independently promotes immune function through various pathways including pathogen recognition, adaptive immune cell activation, and various transcription factors.

Example 7

The OmniGen-AF® composition (Composition I or OG; Prince Agri Products, Inc., Quincy, Ill.) is a branded proprietary product shown to augment immune function in ruminants and other species. Targeted profiling of immune-associated genes in whole blood is an effective platform for identification of multiple immune response markers to feed additives with immune-altering properties. The objective of this study was to identify multiple immune response markers that are increased by dietary OG throughout a 28-d supplementation period. It was hypothesized that several immune-associated genes in whole blood are consistently up-regulated during a 28-d supplementation period. Fourteen male CD rats weighing 180-200 grams had ad libitum access to a diet containing 0 (control; n=5, only 28 days) or 0.5% OG for 7 (n=4) or 28 days (n=5). Whole blood was collected at the end of the feeding period. RNA was purified from whole blood samples and used to generate cDNA that acted as template in the Rat Innate and Adaptive Immune Responses RT$^2$ Profiler PCR array (SABiosciences). Using PROC GLM, we compared cDNA abundance of immune-associated genes between control and supplemented groups (7 or 28 d) with a P<0.05 cut-off value for significance. Of the 77 immune-associated genes that were expressed above the detection limit in all samples, 6 genes were up-regulated after 7 d of OG supplementation and 4 genes were up-regulated after 28 d of OG supplementation. Three genes were up-regulated after 7 d (Cd80: +2.40; Irak1: +2.25; Nod2: +2.08 fold-change) as well as after 28 d of OG supplementation (Cd80: +1.77; Irak1: +2.50; Nod2: +1.83 fold-change). The results suggest Cd80, Irak1, and Nod2 as immune response markers that are increased by dietary OG throughout a 28-d supplementation period.

Example 8

This study was designed to determine the effect of supplementing feedlot steers with the OmniGen-AF® composition (Composition I, OG) on the acute phase response to a lipopolysaccharide (LPS) challenge. Steers (n=18; 270±5 kg BW) were separated into two treatment groups (n=9/treatment): one group was fed a standard receiving diet (Control, Cont) and the other group was fed the same receiving diet supplemented with OG at 4 g/45.4 kg BW for 29 d (OG). On d27 steers were fitted with indwelling jugular cannulas and rectal temperature (RT) monitoring devices and placed in individual stalls. On d28, steers were challenged i.v. with LPS (0.5 µg/kg BW at 0 h). Sickness behavior scores (SBS) and two whole blood samples were collected at 30-min intervals from −2 to 8 h relative to the challenge at 0 h. One vacutainer containing EDTA was collected for complete blood cell count (CBC) analysis, and the second was collected in 9-mL monovette serum tube; after collection serum was isolated and stored at −80° C. until analyzed for cortisol and cytokine concentrations. Rectal temperature, SBS, and cortisol were affected by time (P<0.001). Prior to the challenge, RT was greater (P<0.001) in Cont steers (39.31±0.03° C.) than OG steers (39.14±0.03° C.). Therefore, post-challenge RT was analyzed as the change in response from baseline values. The change in RT relative to baseline values increased (P<0.001) in both groups in response to LPS challenge, but was not affected by treatment (P=0.49). Sickness behavior scores increased (P<0.001) after LPS challenge and tended (P=0.09) to be greater in Control (1.57±0.02) than OG steers (1.51±0.02). Cortisol concentrations were affected by treatment (P=0.005) and time (P<0.001). For both groups, cortisol increased (P<0.001) in response to LPS challenge. Cortisol was greater in Cont (25.2±0.9 ng/mL) than OG steers (25.5±0.9 ng/mL). White blood cell and lymphocyte concentrations were greater (P<0.004) in Cont than OG steers throughout the study. Neutrophils were decreased (P=0.04) in Cont steers (0.7±0.2 K/uL) compared to OG steers (1.3±0.2 K/uL) prior to the LPS challenge. There was a treatment (P<0.02) and time (P<0.001) effect for tumor necrosis factor-α (TNFα) and interferon-γ (IFNγ). Specifically, TNFα and IFNγ concentrations increased (P<0.001) in response to LPS challenge. Furthermore, concentrations of TNFα and IFNγ were decreased in (P≤0.02) in Cont steers compared to OG steers. These data suggest that OG supplementation served to prime the immune system prior to the LPS challenge, allowing for an enhanced response to LPS challenge.

Example 9

The use of probiotic feed supplements to enhance animal health and growth are of great interest to the beef industry. Studies have demonstrated that some probiotic supplements may affect metabolism, and therefore influence an animal's response to an immune challenge. This study was designed to determine the effect of supplementing feedlot steers with OmniGen-AF® composition (Composition I, OG) during the receiving period on the metabolic response to a lipopolysaccharide (LPS) challenge. Steers (n=18; 270±5 kg BW) were obtained and transported to the feedlot. Upon arrival steers were processed and separated into 2 treatment groups (n=9/treatment): one group was fed a standard receiving diet (Control; Cont) and the other group was fed the same receiving diet supplemented with the OmniGen-AF® composition at 4 g/45.4 kg BW/d for 29 d (OG). On d 27 steers were fitted with indwelling jugular cannulas and placed in individual stalls. On d 28, steers were challenged i.v. with LPS (0.5 µg/kg BW at 0 h) and blood samples were collected at 30-min intervals from −2 to 8 h and at 24 h post-challenge. Serum was isolated and stored at −80° C. until analyzed for glucose, non-esterified fatty acids (NEFA) and blood urea nitrogen (BUN) concentrations. Glucose concentrations were affected by treatment (P=0.009) and time (P<0.001). Glucose was greater in OG steers compared to Cont steers (76.4±1.1 mg/dL vs. 72.4±1.0 mg/dL). For NEFA concentrations, there was a treatment (P<0.001) and time (P<0.001) effect. Specifically, Cont (0.210±0.007 mmol/L) steers had greater NEFA concentrations than OG steers (0.101±0.010 mmol/L). There was a tendency (P=0.07) for a treatment× time interaction such that NEFA concentrations were greater (P<0.03) in Cont steers than OG steers from 3 to 8 hr after LPS challenge. For BUN, there was a treatment (P<0.001) effect such that concentrations were greater in Cont steers (12.4±0.1 mg/dL) than OG supplemented steers (11.5±0.1 mg/dL) throughout the study, and were not affected by time (P=0.28). These data suggest that OG supplementation modulates the metabolic response to a LPS challenge and provides an indication that supplementation of feedlot steers with OG may prevent the breakdown of other substrates (e.g., protein and fat) for energy during an immune challenge.

In view of the many possible embodiments to which the principles of the disclosed technology may be applied, it should be recognized that the illustrated embodiments are only preferred examples of the technology and should not be taken as limiting the scope of the technology. Rather, the scope of the technology is defined by the following claims. We therefore claim as our invention all that comes within the scope and spirit of these claims.

We claim:

1. A method, comprising:
   identifying a bovine that is at risk of experiencing a heat effect;
   assessing a bovine's initial water consumption, a bovine's initial respiration rate, or both the bovine's initial water consumption and the bovine's initial respiration rate; and
   administering to the bovine a composition comprising between 1.0 wt % and 5.0 wt % β-glucans, between 15 wt % and 40 wt % silica, between 50 wt % and 81 wt % mineral clay, between 1 wt % and 8.0 wt % mannan, and endoglucanohydrolase, wherein the composition is administered for an effective period of time of from 7 days to 200 days to decrease the bovine's water consumption, the bovine's respiration rate, or both the bovine's water consumption and the bovine's respiration rate during the effective period of time, when compared to the bovine's initial water consumption, the bovine's initial respiration rate, or both the bovine's initial water consumption and the bovine's initial respiration rate prior to administering the composition.

2. The method of claim 1, wherein the bovine is a dairy cow.

3. The method of claim 2, further comprising administering the composition to the dairy cow:
   (a) for a period from 100 days prior to lactation onset to 1 day prior to lactation onset; or
   (b) after lactation onset; or
   (c) for 40 days to 100 days post calving; or
   (d) any combination thereof.

4. The method of claim 1, further comprising administering the composition to the bovine when a temperature humidity index is, or is expected to be, greater than 68.

5. The method of claim 1, further comprising administering to the bovine a therapeutic process, a therapeutic agent, or a combination thereof, wherein the therapeutic process or therapeutic agent is provision of shade to the bovine, use of a water sprinkler to externally administer water to the bovine, use of a fan to provide air movement, addition of bypass fats to feed for the bovine, meloxicam, a corticosteroid, a composition comprising one or more electrolytes, an alkalinizing agent, a direct-fed microbial, or a combination thereof.

6. The method of claim 1, further comprising:
   administering the composition to individual bovines in a group of bovines for a first period of time;
   subsequently evaluating water consumption, respiration rate, or both the water consumption and the respiration rate of at least one bovine of the group of bovines; and
   administering an adjusted amount of the composition to the group of bovines for a subsequent period of time, wherein the adjusted amount is based at least in part on the subsequent evaluation of the water consumption, the respiration rate, or both the water consumption and the respiration rate.

7. The method of claim 1, further comprising:
   increasing an amount of the composition administered to the bovine to an increased amount if a temperature humidity index is expected to increase to 68 or greater; or
   decreasing an amount of the composition administered to the bovine to a decreased amount if a temperature humidity index is expected to decrease below 68, wherein the decreased amount of the composition is at least 50 grams per head per day.

8. The method of claim 1, wherein the effective period of time is at least 30 days, the method further comprising administering the composition at set intervals to the bovine.

9. The method of claim 8, wherein the composition is administered daily to the bovine.

10. The method of claim 1, wherein the composition further comprises a carbonate, kelp, niacin, vitamin B-12, biotin, d-calcium pantothenate, choline chloride, thiamine mononitrate, pyridoxine hydrochloride, menadione dimethylpyrimidinol bisulfite, riboflavin-5-phosphate, folic acid, soybean oil, calcium aluminosilicate, rice hulls, mineral oil, or any combination thereof.

11. A method, comprising:
   identifying a bovine that is at risk of experiencing a heat effect and that has been administered a first amount of a composition comprising between 1.0 wt % and 5.0 wt % β-glucans, between 15 wt % and 40 wt % silica, between 50 wt % and 81 wt % mineral clay, between 1 wt % and 8.0 wt % mannan, and endoglucanohydrolase for a time period of from 7 days to 200 days, the bovine having a first water consumption, a first respiration rate, or a first water consumption and a first respiration rate that are decreased relative to the bovine's water consumption, the bovine's respiration rate, or both the bovine's water consumption and the bovine's respiration rate prior to administering the first amount of the composition;
   monitoring the bovine during a subsequent period of heat stress; and
   administering to the bovine a second amount of the composition that is greater than the first amount, the second amount being sufficient to maintain or reduce the bovine's water consumption, the bovine's respiration rate, or both the bovine's water consumption and the bovine's respiration rate, such that the bovine's water consumption, the bovine's respiration rate, or both the bovine's water consumption and the bovine's respiration rate subsequent to administration of the second amount are substantially the same as the first water consumption, the first respiration rate, or both the first water consumption and the first respiration rate.

12. The method of claim 11, wherein the first amount is at least 50 grams per head per day and the second amount is greater than the first amount and up to 70 grams per head per day.

13. The method of claim 1, wherein the composition is administered to the bovine for an effective period of time to decrease water consumption during the effective period of time, when compared to the bovine's water consumption prior to administering the composition.

14. The method of claim 1, wherein the composition is administered to the bovine for an effective period of time to decrease the bovine's respiratory rate during the effective period of time, when compared to the bovine's respiratory rate prior to administering the composition.

* * * * *